(12) United States Patent
Ganz et al.

(10) Patent No.: US 6,360,792 B1
(45) Date of Patent: Mar. 26, 2002

(54) AUTOMATED MICROPLATE FILLING DEVICE AND METHOD

(75) Inventors: Brian L. Ganz, Carlsbad; John Andrew Moulds, Encinitas; Christopher T. Brovold, Carlsbad, all of CA (US)

(73) Assignee: RoboDesign International, Inc., Carlsbad, CA (US)

( * ) Notice: Subject to any disclaimer, the term of this patent is extended or adjusted under 35 U.S.C. 154(b) by 0 days.

(21) Appl. No.: 09/702,164

(22) Filed: Oct. 30, 2000

Related U.S. Application Data

(63) Continuation-in-part of application No. 09/411,943, filed on Oct. 4, 1999, now Pat. No. 6,148,878.

(51) Int. Cl.⁷ ................................................. B65B 1/04
(52) U.S. Cl. ..................... 141/129; 141/130; 422/100; 422/103; 436/180
(58) Field of Search ................................. 141/129, 130, 141/1; 422/99, 100, 103; 436/174, 180

(56) References Cited

U.S. PATENT DOCUMENTS 6,148,878 A * 11/2000 Ganz et al. ................. 141/129

* cited by examiner

Primary Examiner—Steven O. Douglas
(74) Attorney, Agent, or Firm—John R. Ross; John R. Ross, III

(57) ABSTRACT

An automated machine for filling a plurality of microplates. The automated machine includes at least one input stacking chamber for stacking empty microplates, at least one output stacking chamber for stacking filled microplates, and a microplate filling assembly disposed between the at least one input stacking chamber and the at least one output stacking chamber. The microplate filling assembly has a walking beam indexer, a lid lifter for lifting the lid off each microplate to permit the microplate to be filled, and after filling to replace the lid, and a fill mechanism in communication with a media source and positioned to fill the empty microplates after their lids have been lifted off. An automatic control unit is programmed to cause the walking beam indexer to move empty microplates from the at least one input stacking chamber, to cause the lid lifter to lift the lid off each microplate, to cause the fill mechanism to inject media from the media source into wells in the microplates, to cause the lid lifter to replace the lid after the media is injected, and to cause the walking beam indexer to move the microplates to the at least one output stacking chamber. In a preferred embodiment of the present invention, there are ten input stacking chambers and ten output stacking chambers and they are mounted on an input carousel and output carousel, respectively.

31 Claims, 34 Drawing Sheets

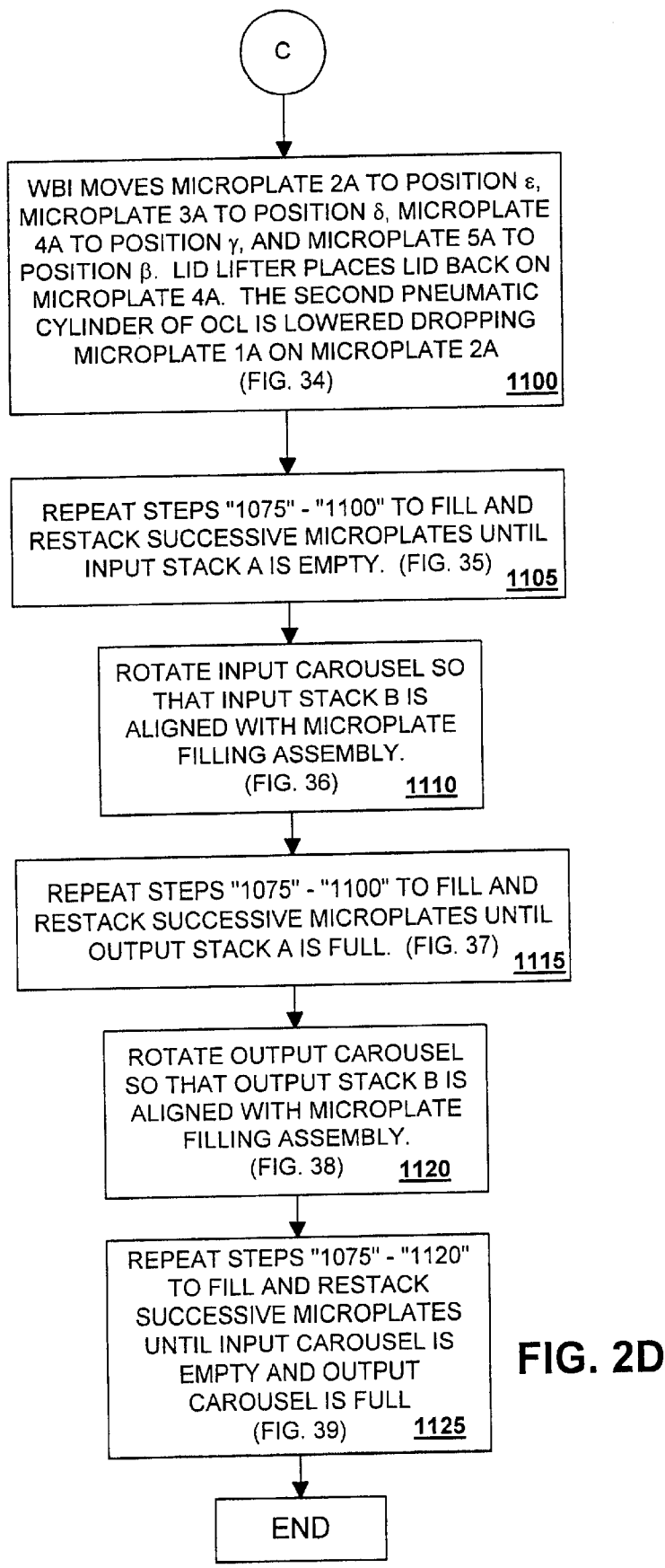

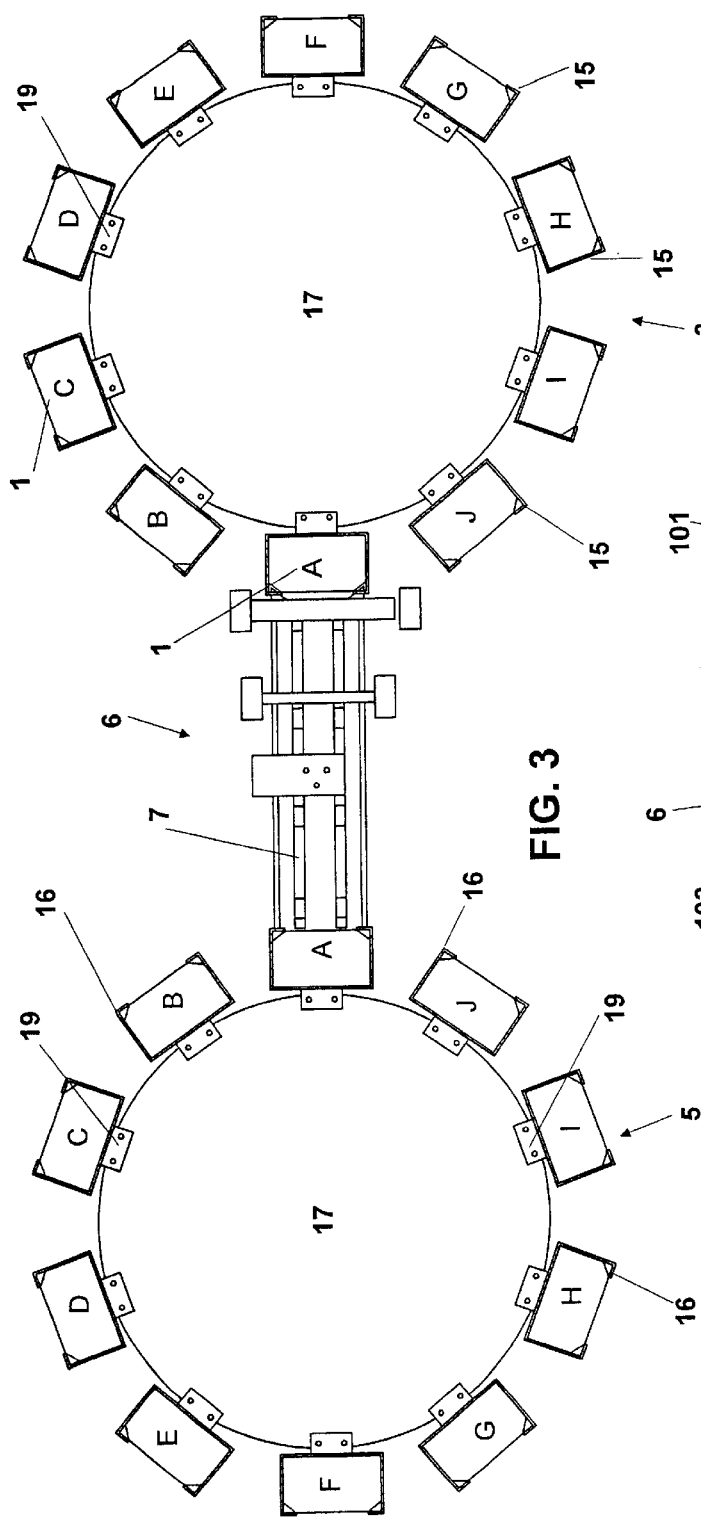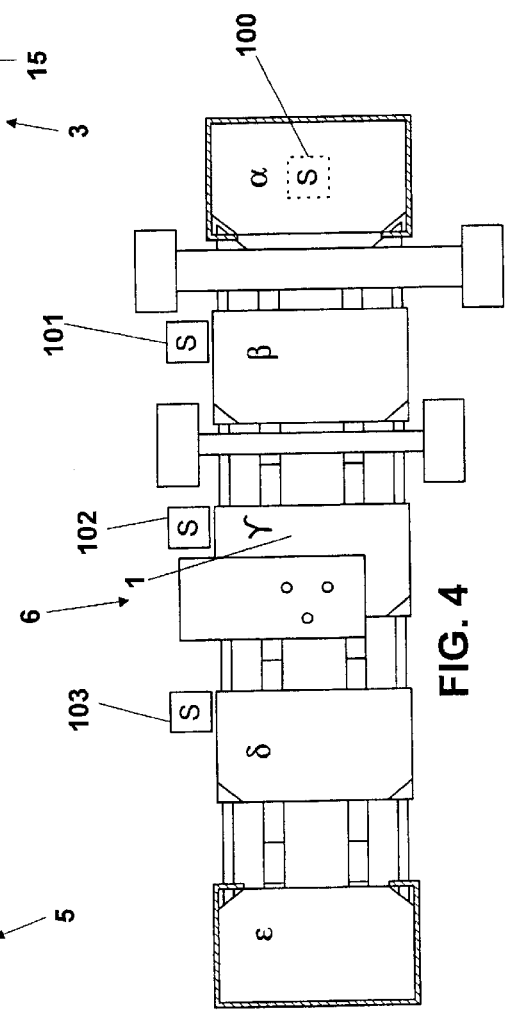

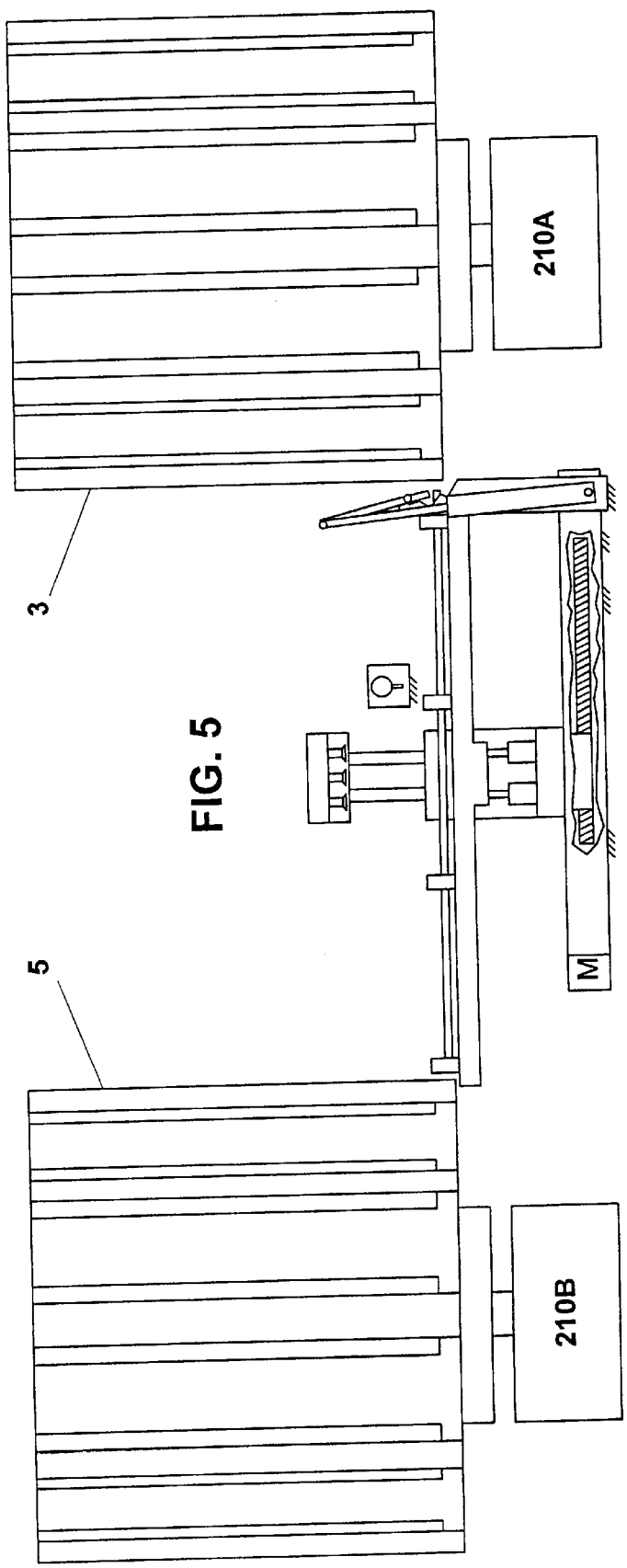

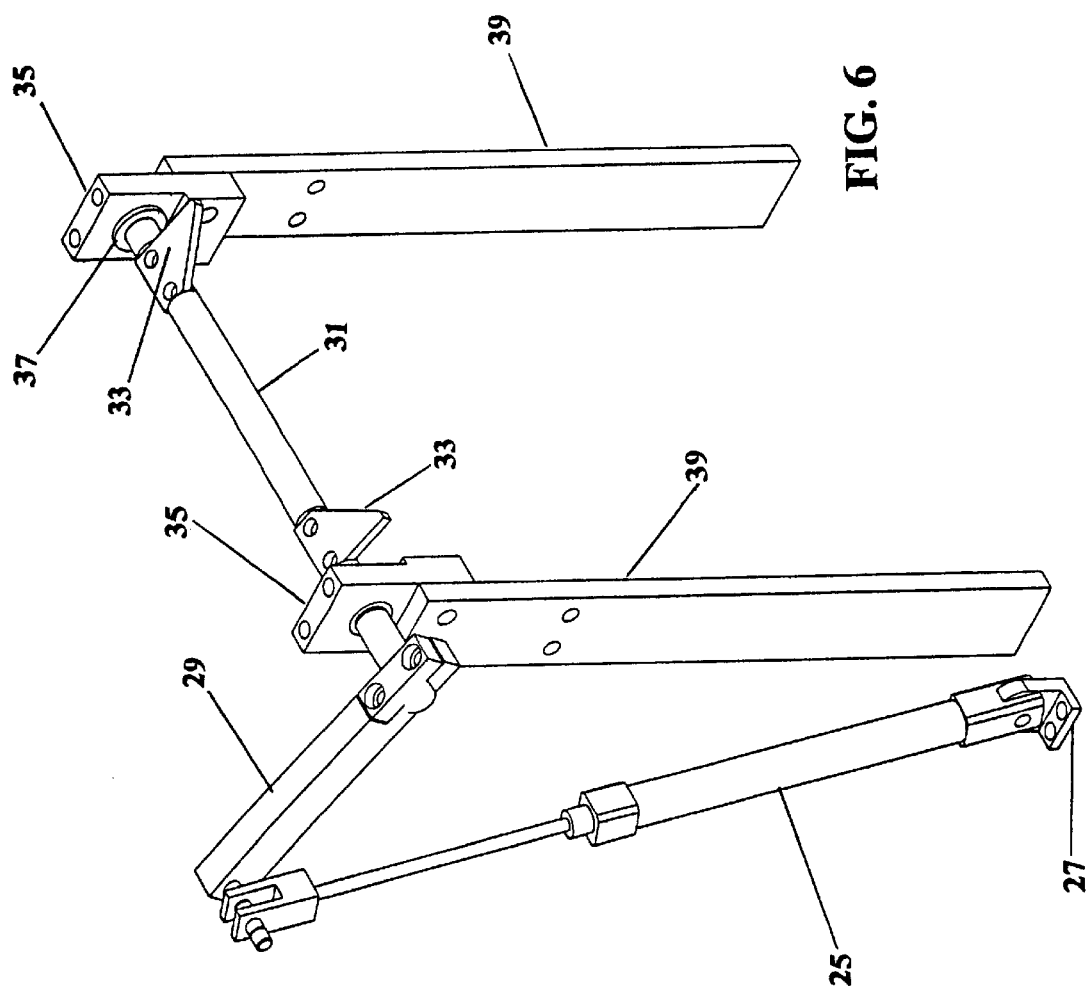

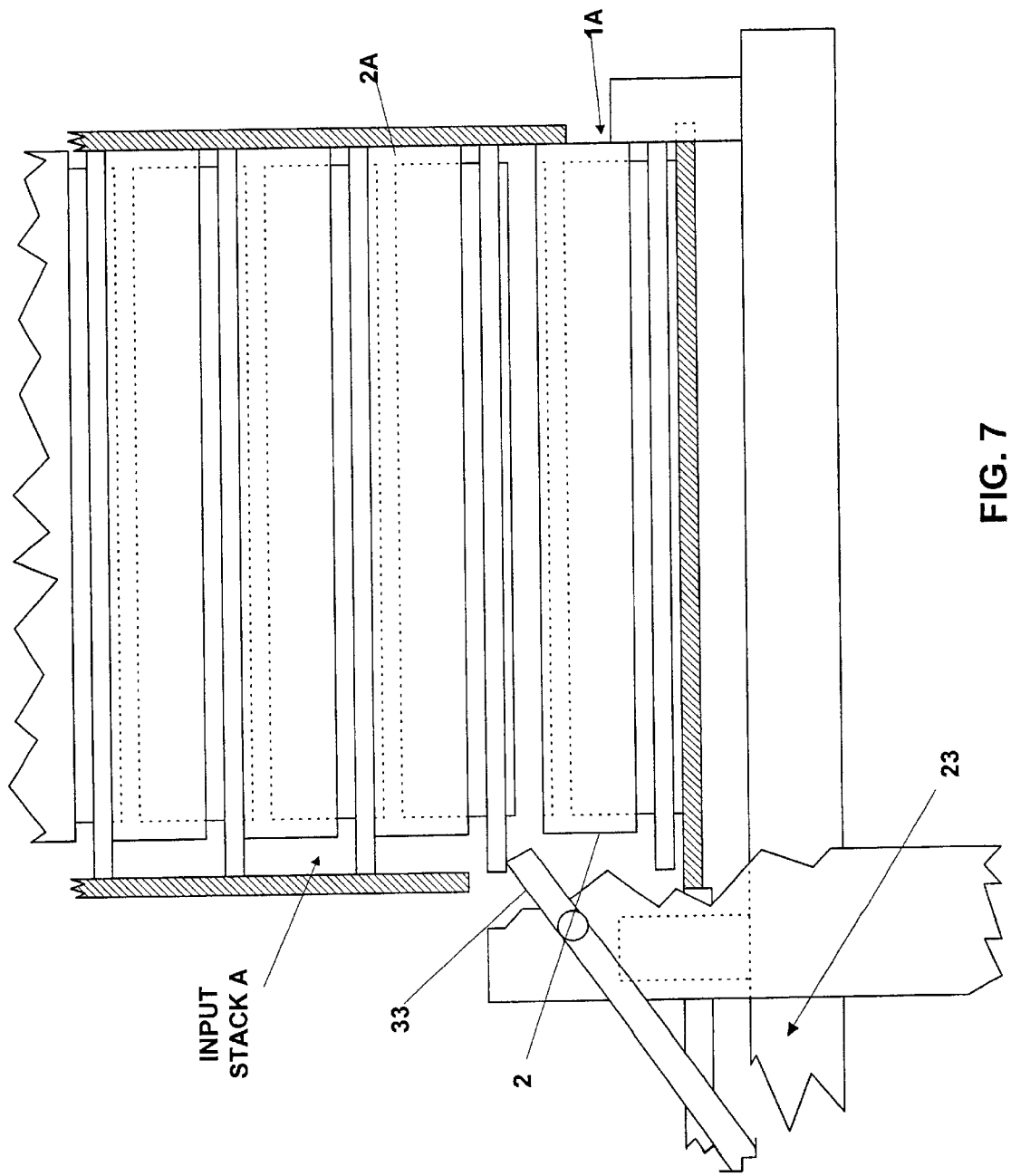

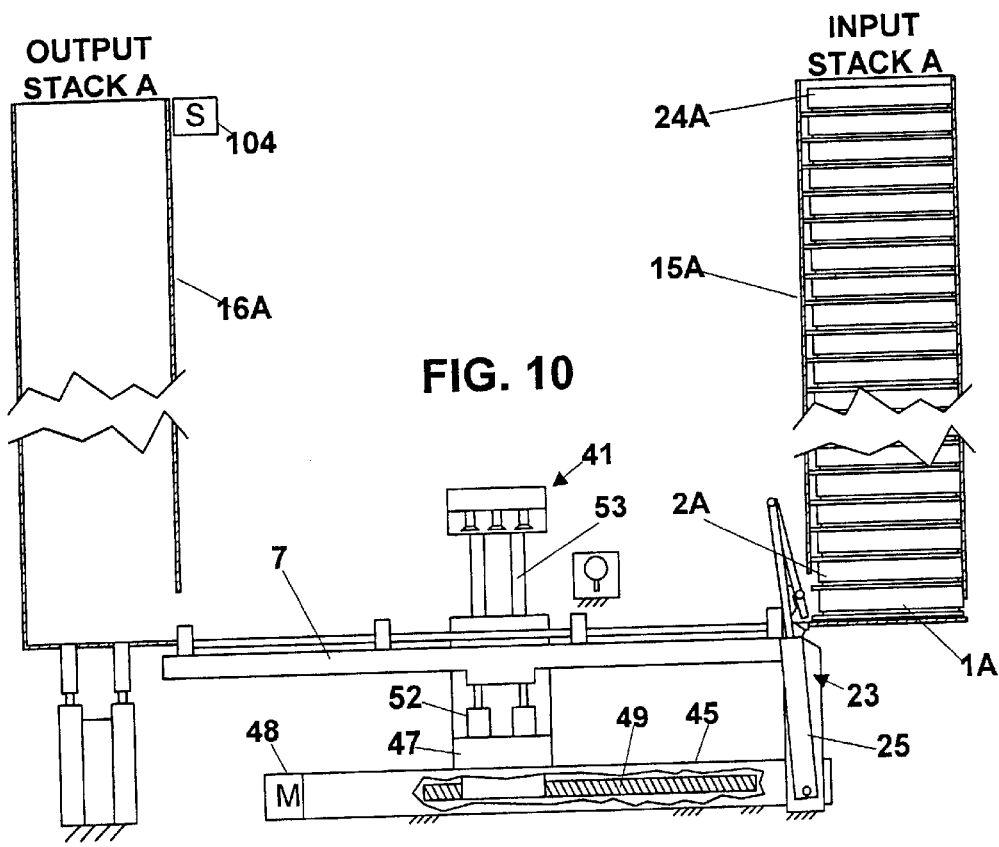
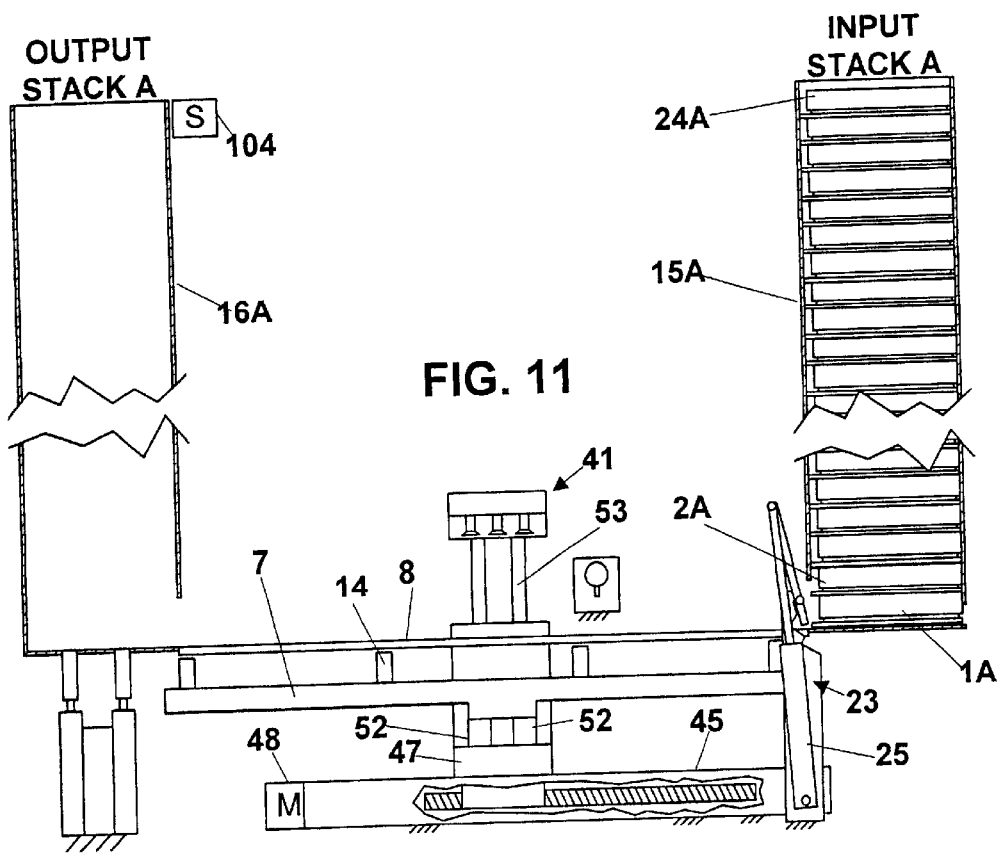

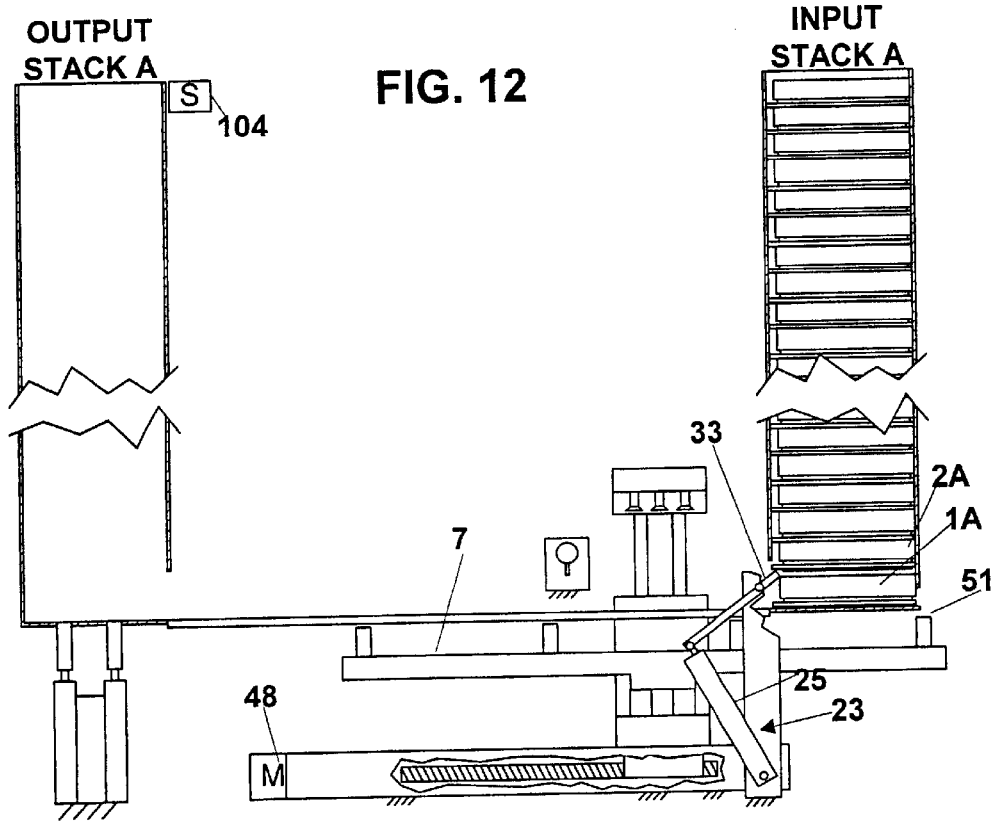
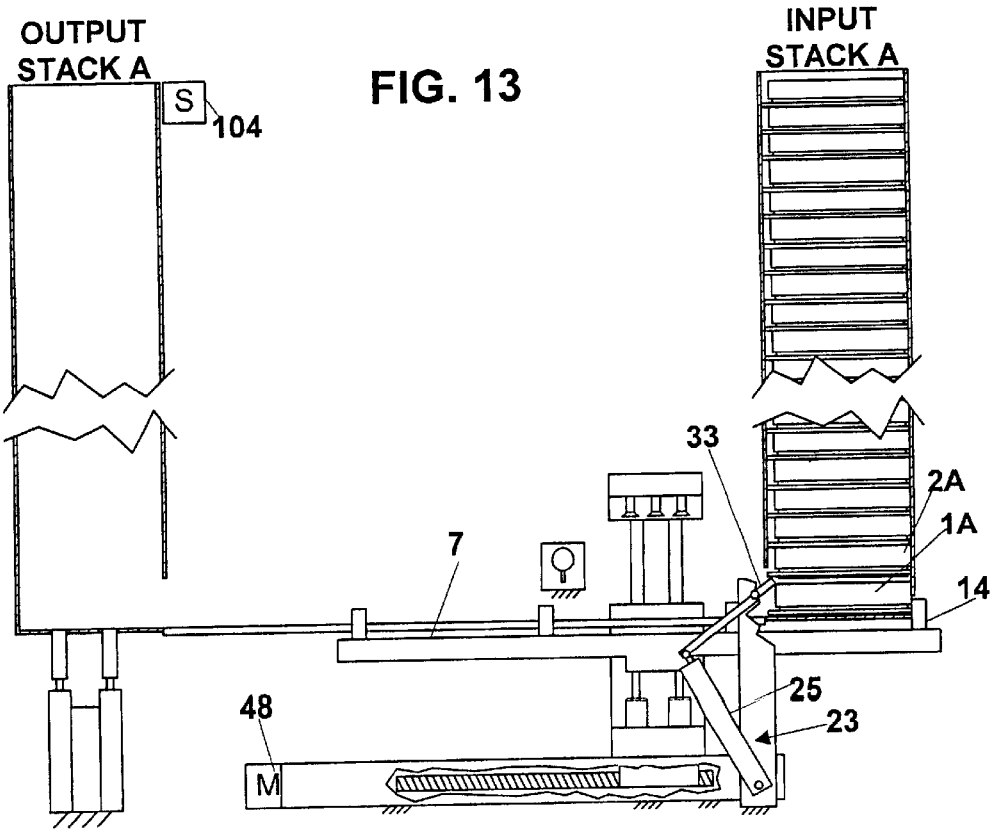

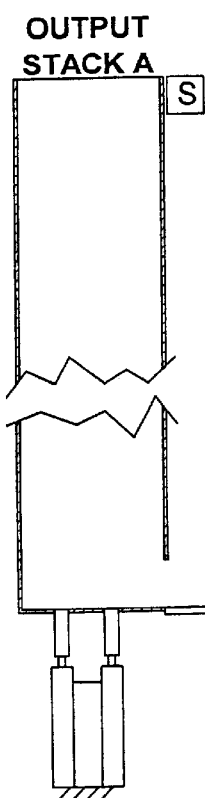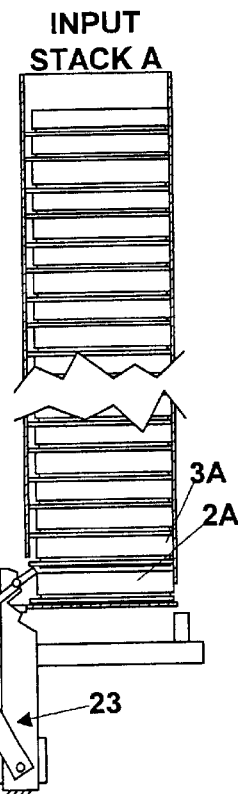
FIG. 16
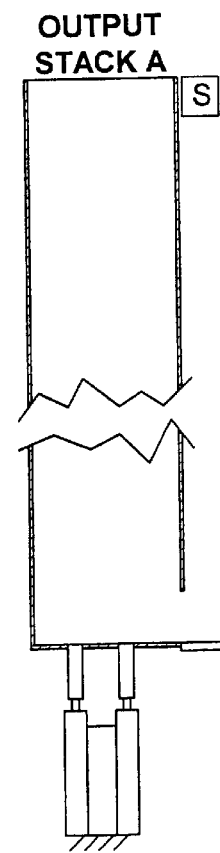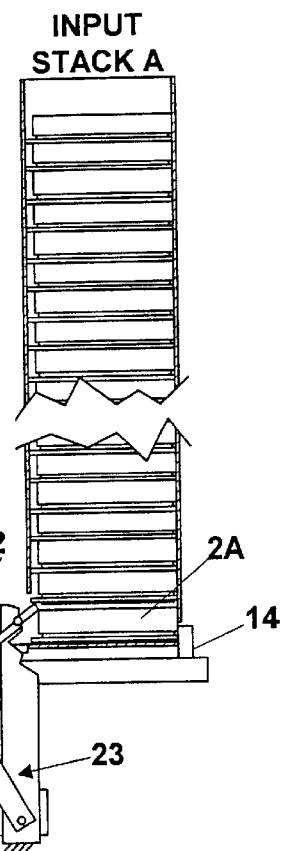
FIG. 17

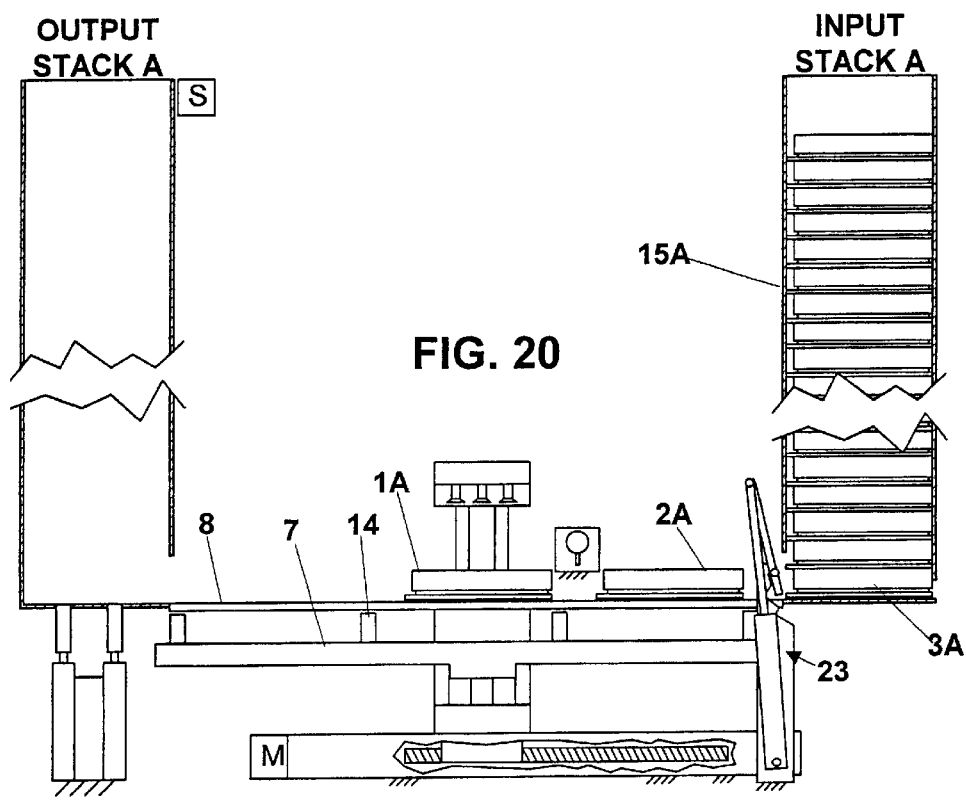
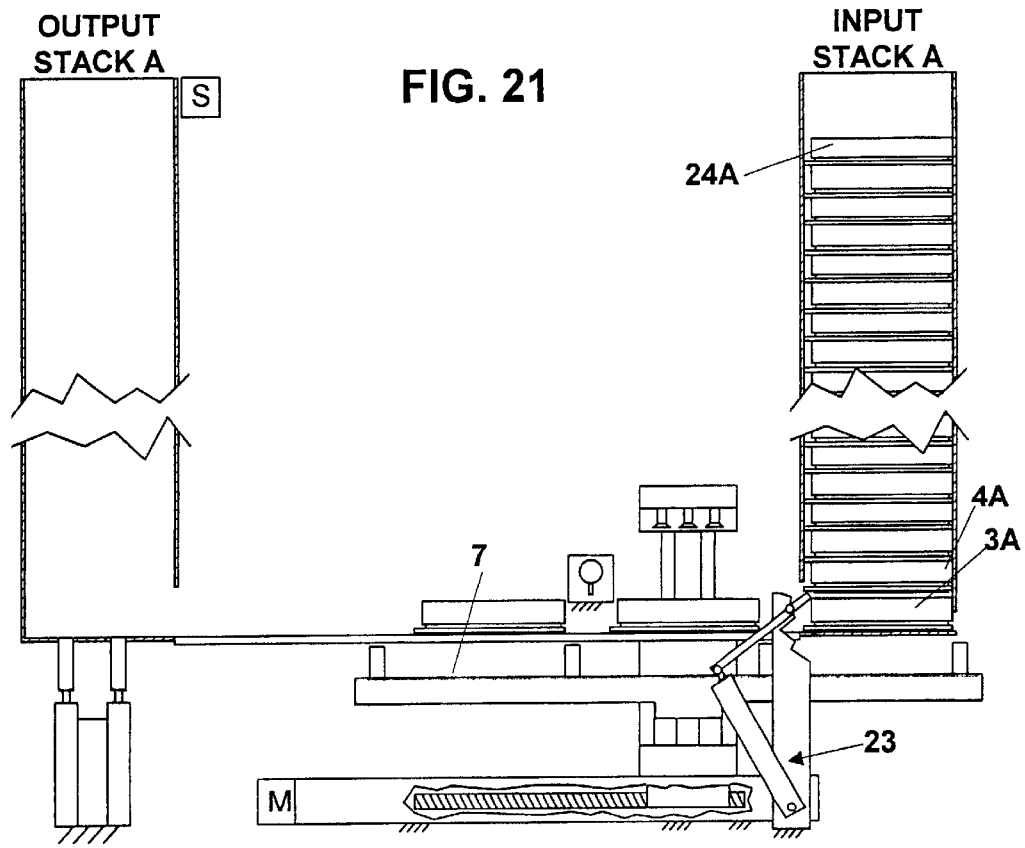

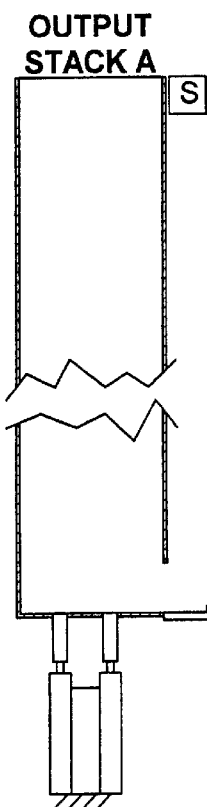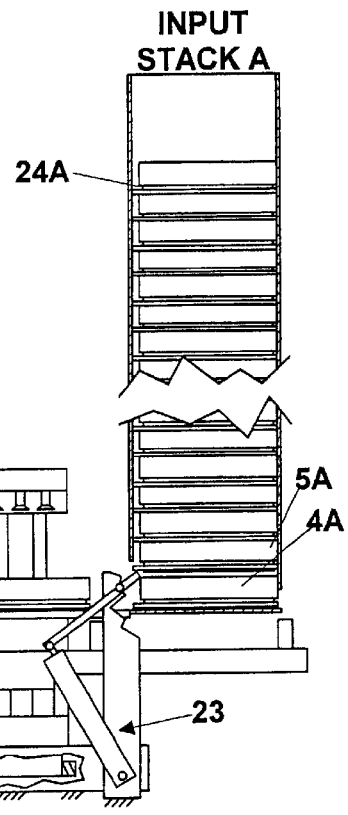
FIG. 26
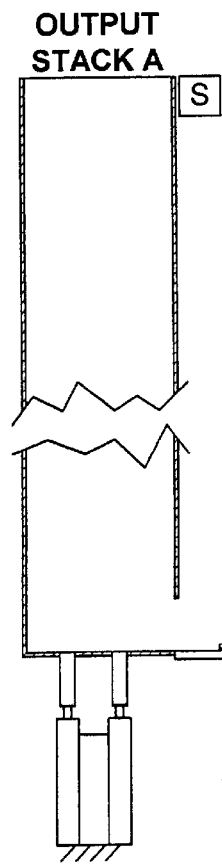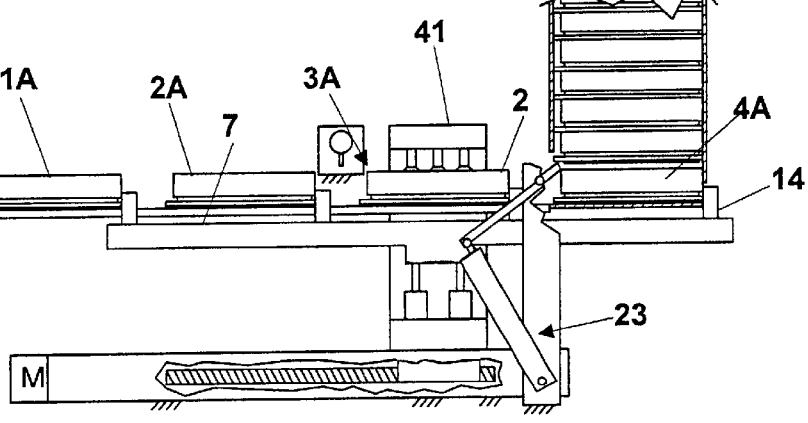
FIG. 27

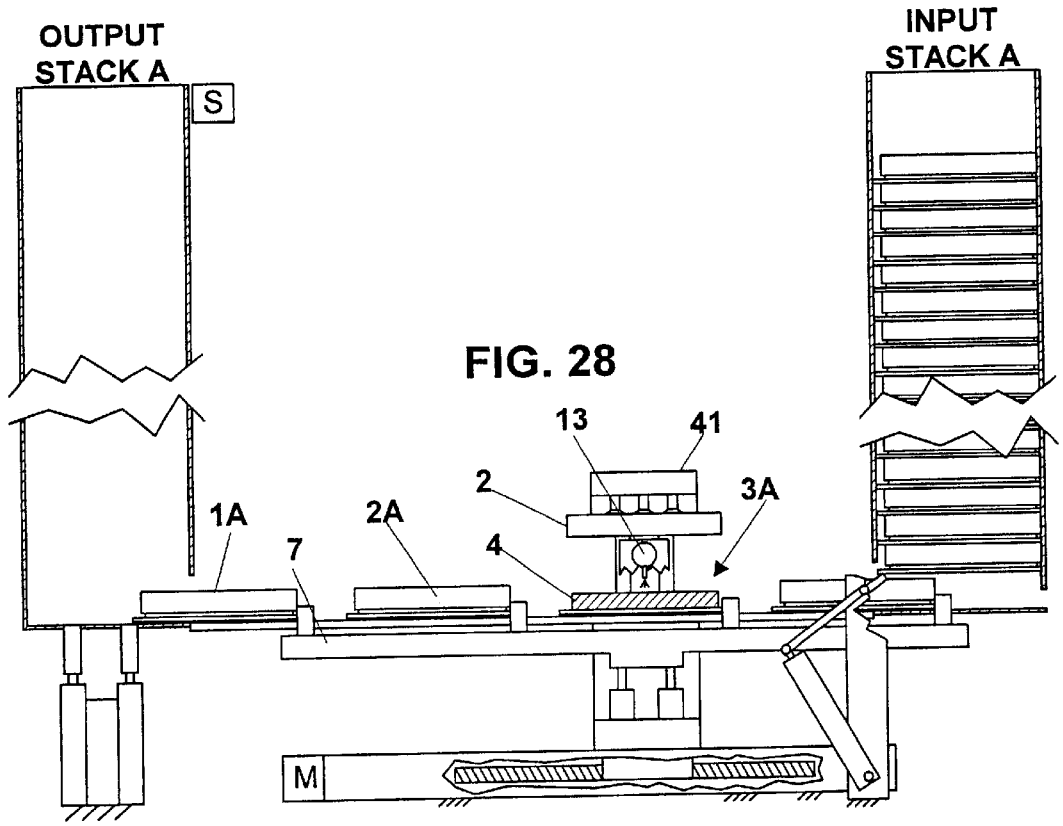
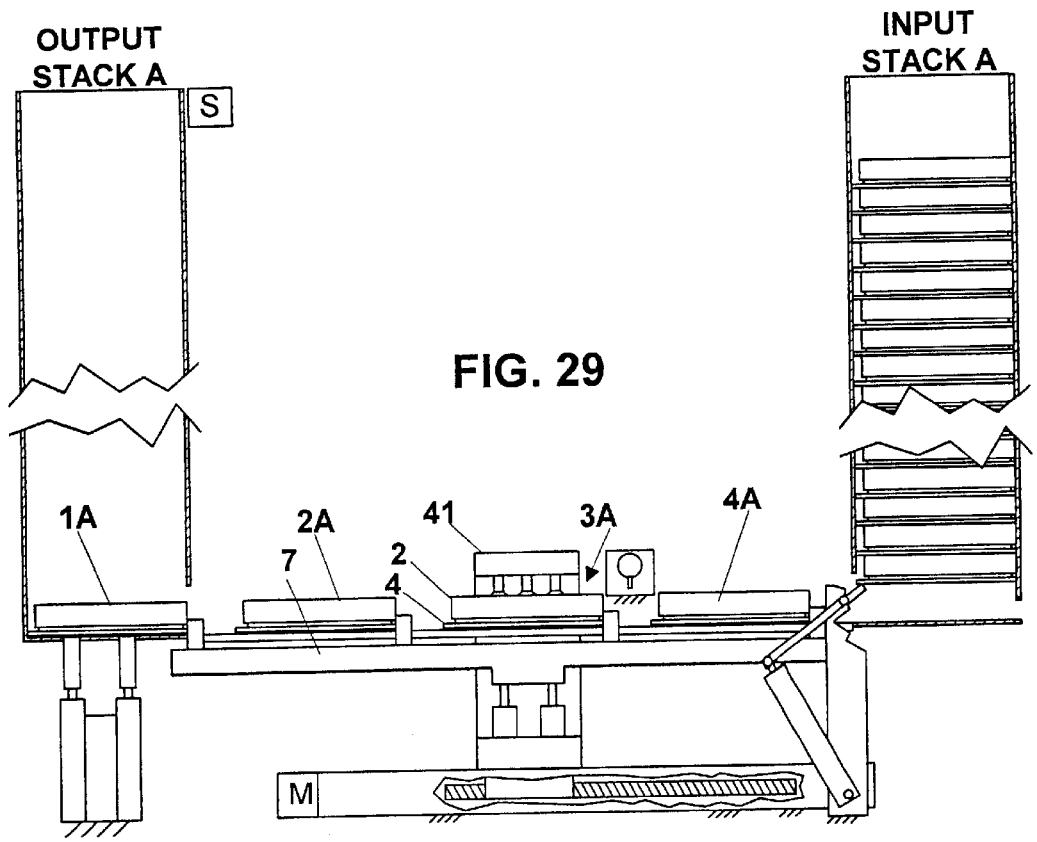

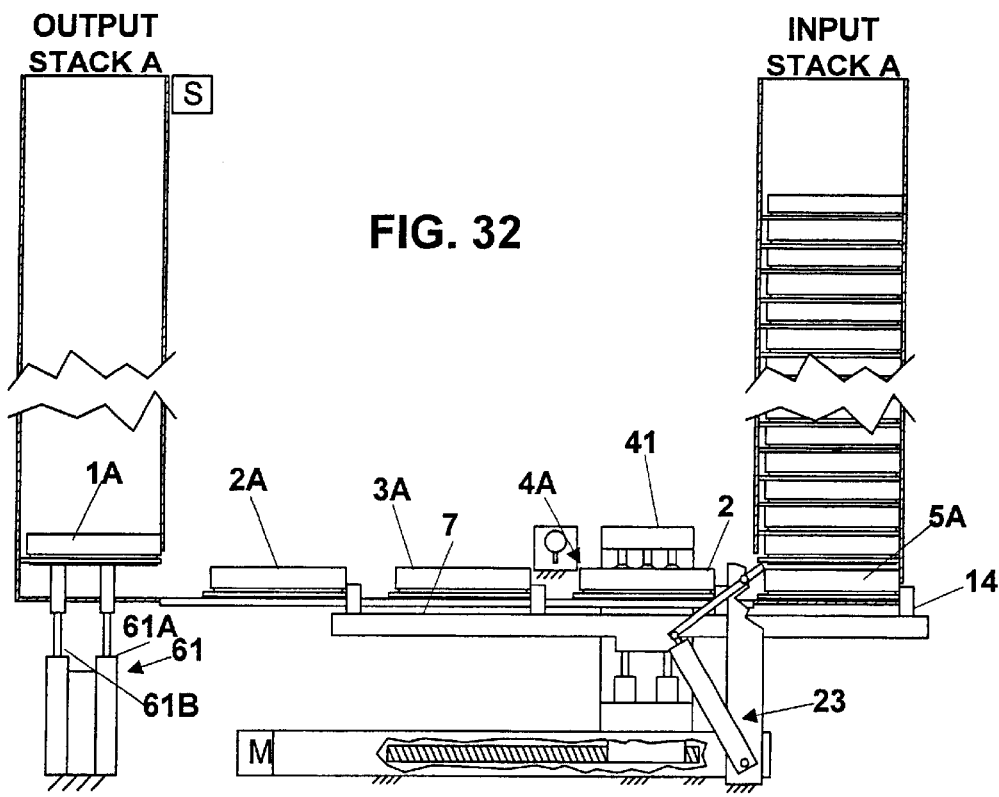
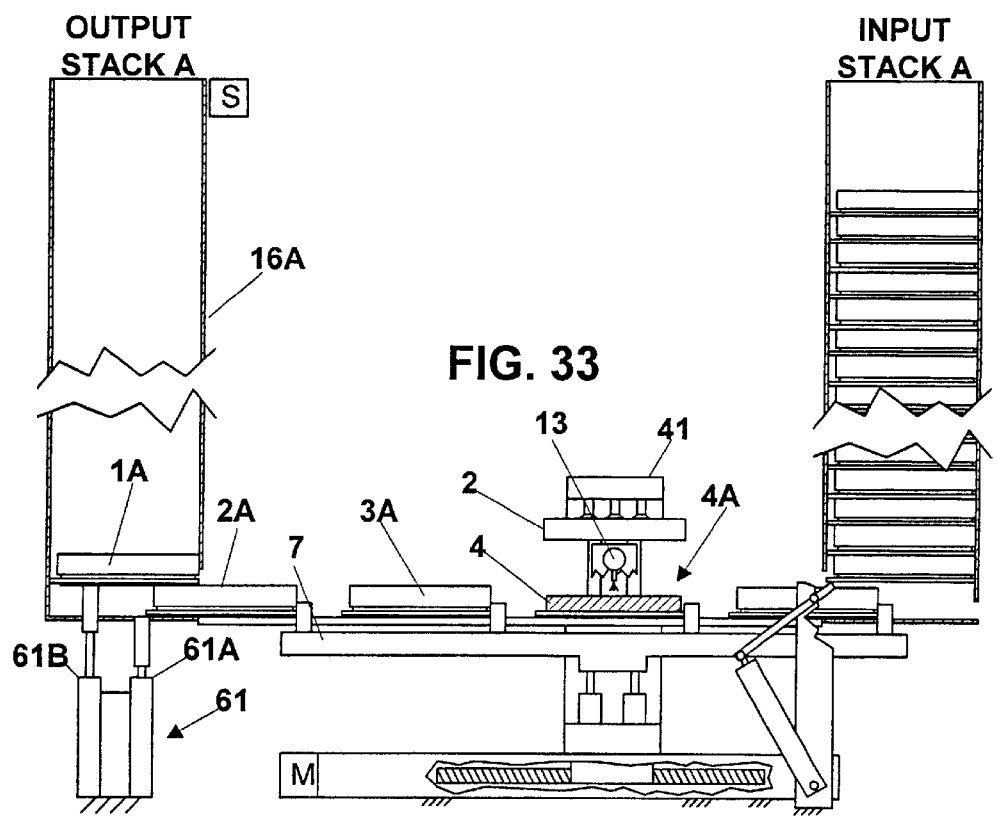

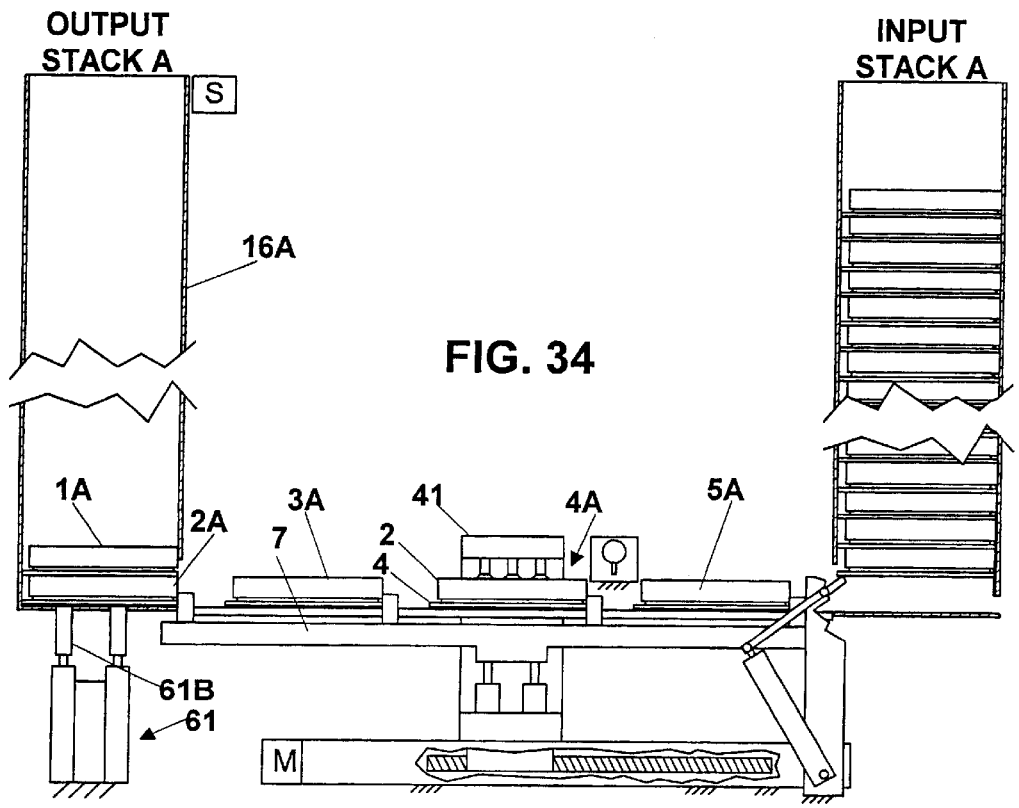
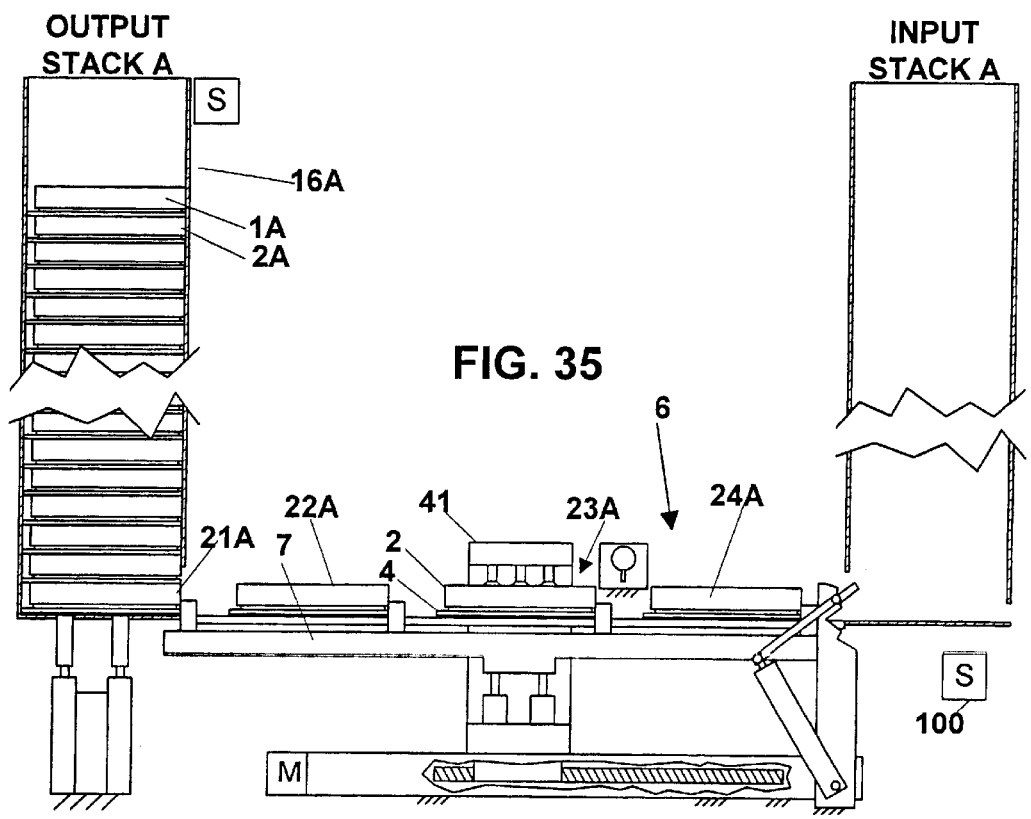

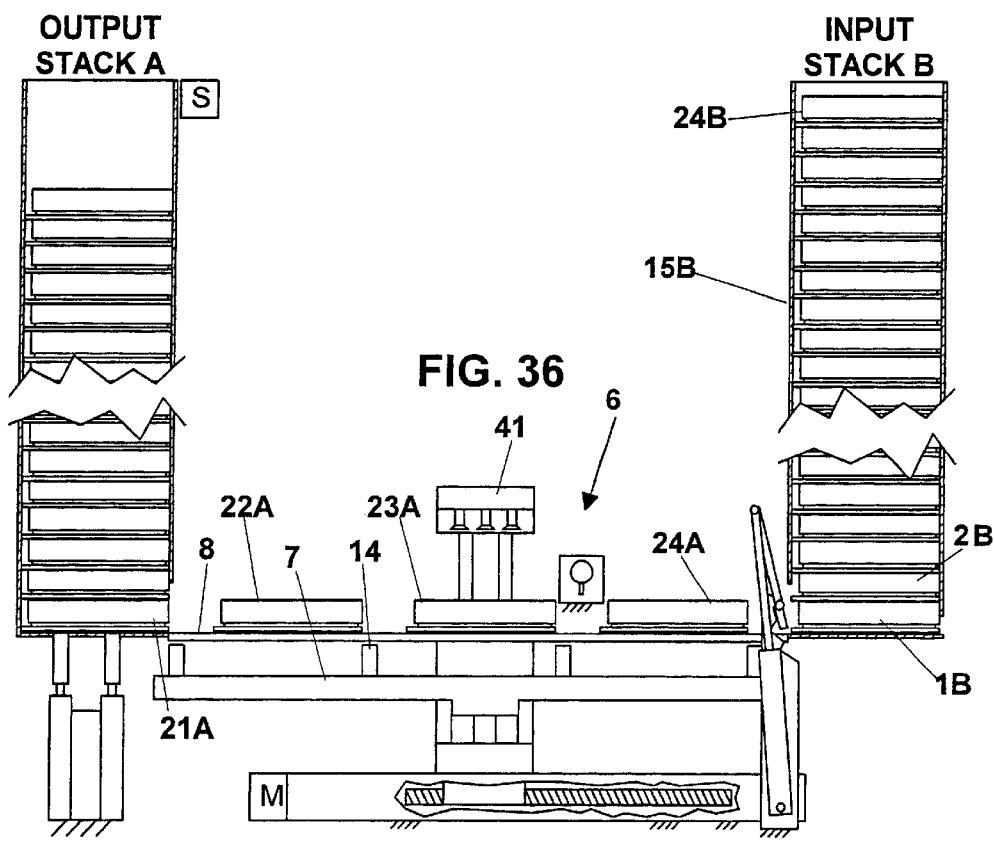
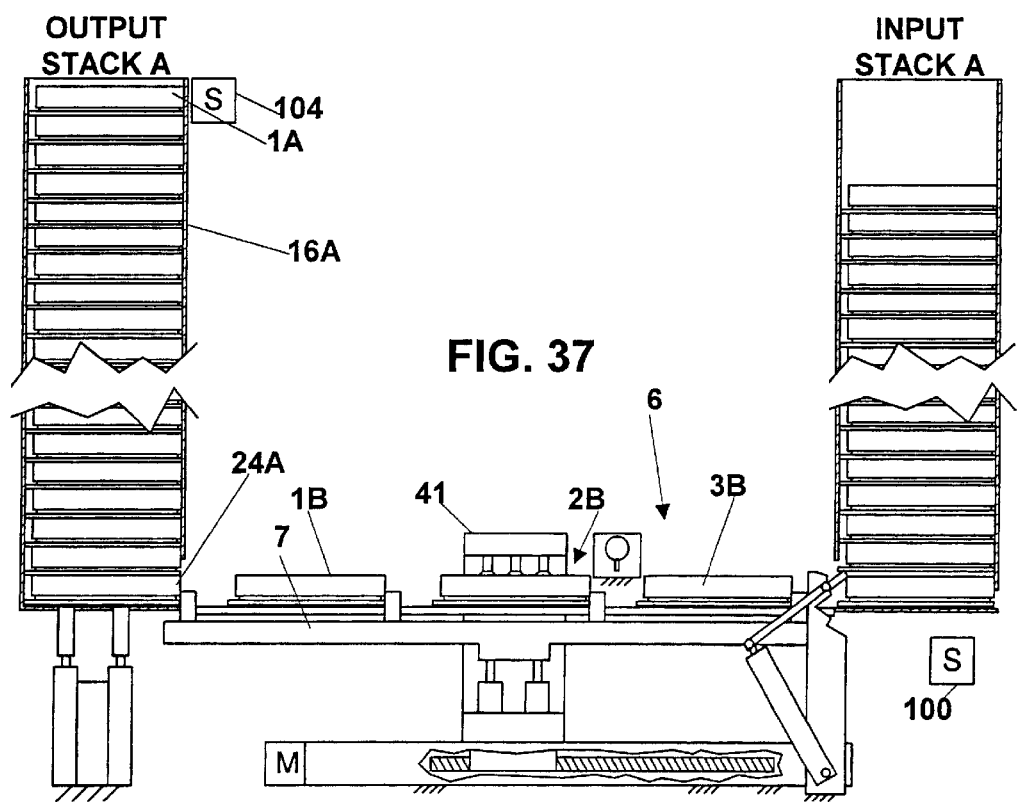

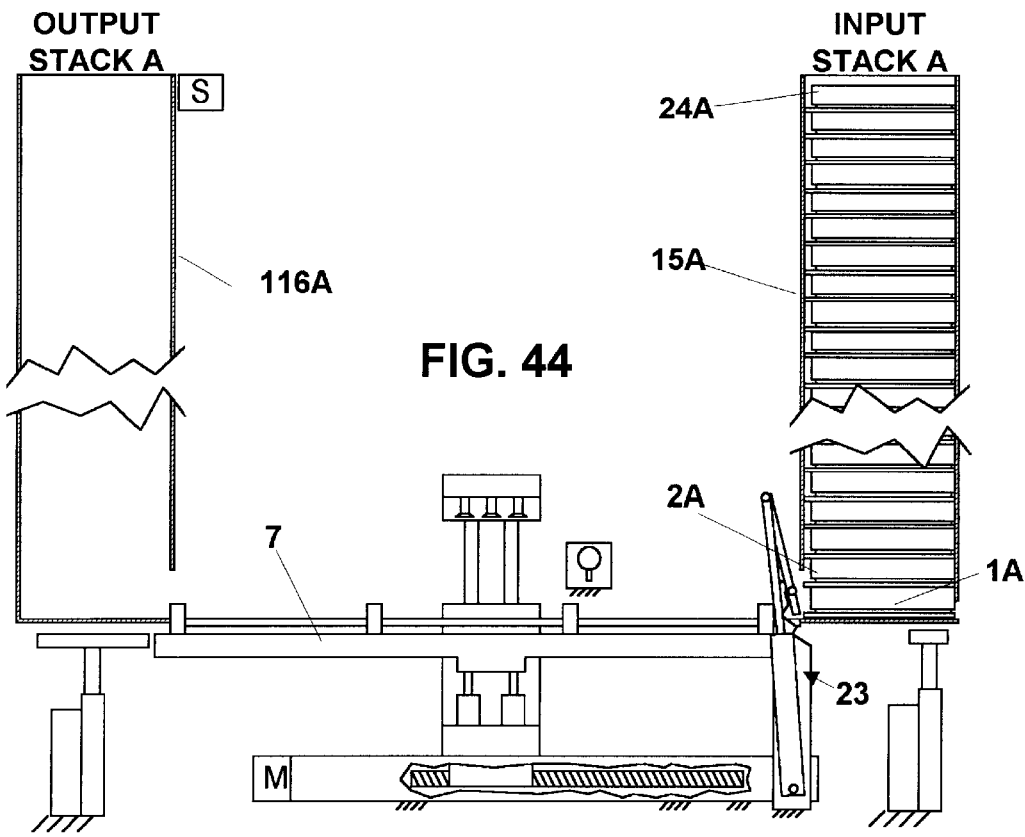
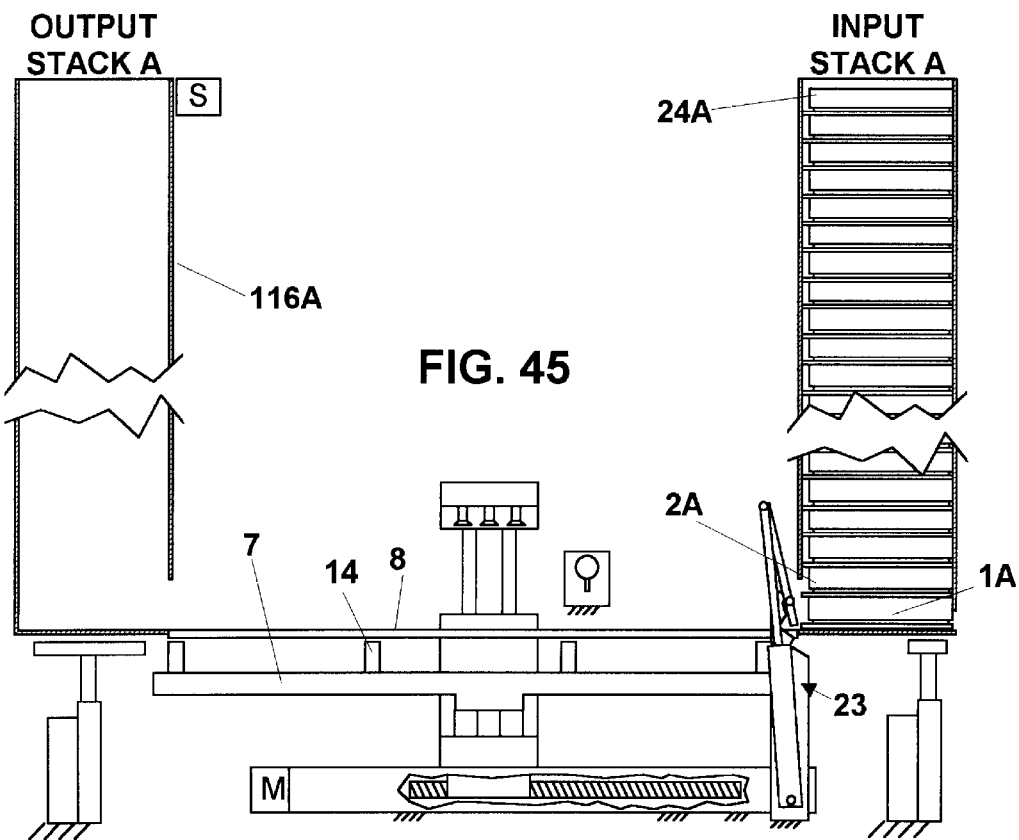

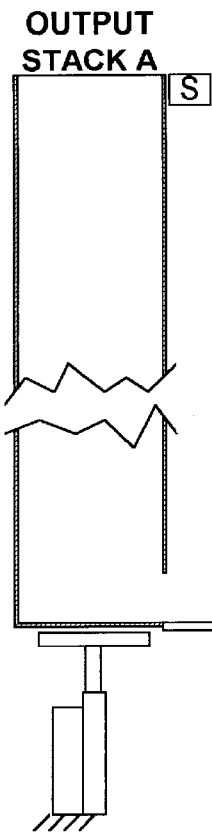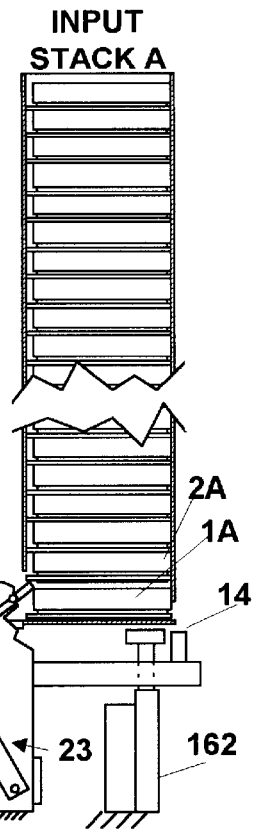
FIG. 46
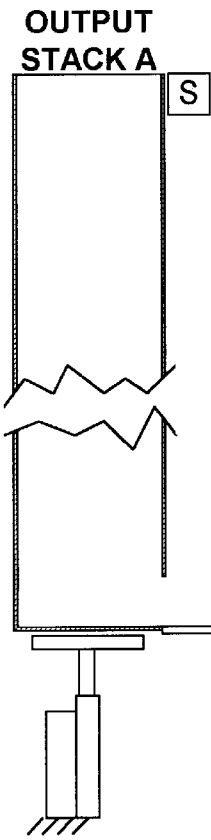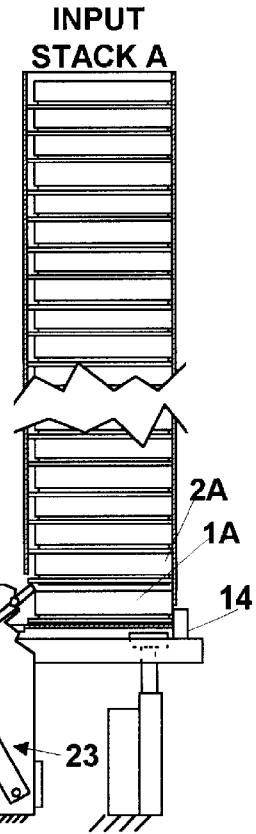
FIG. 47

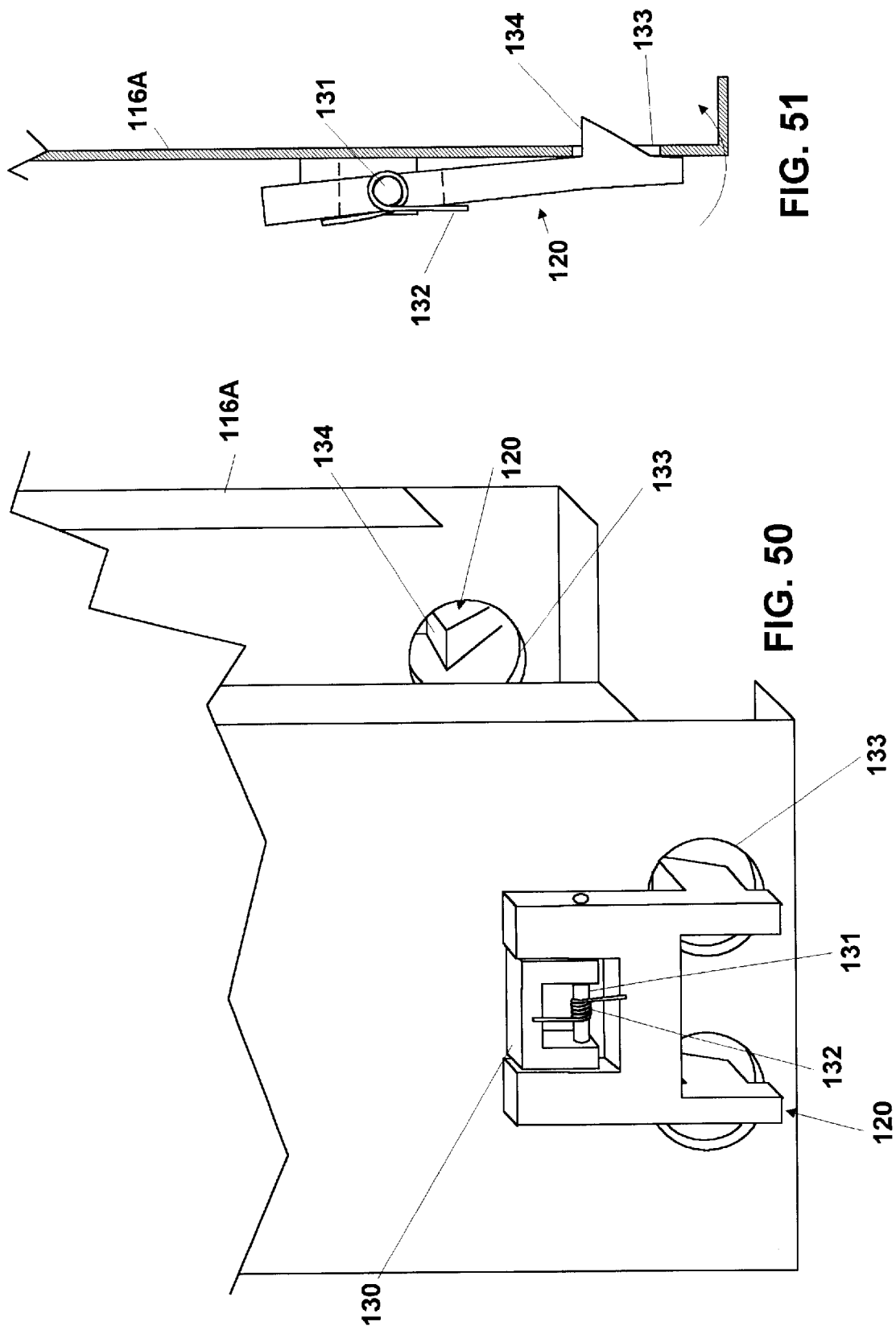

AUTOMATED MICROPLATE FILLING DEVICE AND METHOD

The present invention relates to microplate filling devices, more specifically it relates to automated microplate filling devices. This application is a continuation-in-part of U.S. patent application Ser. No. 09/411,943, filed Oct. 4, 1999, and soon to issue as U.S. Pat. No. 6,148,878.

BACKGROUND OF THE INVENTION

Microplates, also known as micro-well plates, are a standard product and are regularly used in medical, chemical and biological laboratories. A perspective view of a microplate 1 is shown in FIG. 1A. Microplate 1 has microplate lid 2 and microplate base 4. Microplate 1 shown in FIG. 1A and 1B has just one well. FIG. 1C shows a microplate with 96 wells in its base 4 and FIG. 1D shows a microplate with 384 wells in its base 4. Microplates with 1536 wells are also available.

In the laboratory, microplates are commonly filled with various media. The media can be either in a liquid form or have a thicker, viscous consistency, such as that found in Agar. It is very important to the efficient productivity of a laboratory to be able to pour media into microplates accurately and rapidly. In order to produce a high volume of prepared microplates, an automated machine can provide the required throughput much faster than a technician can. To this end there are several automated devices that are currently available that will automatically fill microplates with media. Thermo Vision, Inc. with offices in Grand Junction Colorado, makes an automated filling machine that can only handle ten plates at a time and must be monitored continuously to remove filled plates and add new ones. Zymark Corp., with offices in Hopkinton Mass., produces a liquid handling workstation, but it is also for low capacity runs and requires constant supervision. A automated filling machine is known that has slightly greater capacity than those made by Thermo Vision and Zymark Corp., but the increased capacity is limited on the input side and there is no restacking capability. This means that there has to be a technician present at all times to remove filled plates and make room for the new ones. This machine also uses an expensive robot for positioning. The robot adds extra cost to the device. CCS Packard, with offices in Torrance Calif., produces a couple of machines that include both an input and an output chamber that can hold up to 50 plates. These devices rely on a conveyor system.

The main problems with the above known devices are that they are very expensive and must be monitored at all times due to low capacity and/or no input/output unstacking and restacking capabilities.

In order to save money, there have been attempts to make manual microplate filling machines. U.S. Pat. No. 5,415,060 discloses a device in which a bridge that aligns and holds steady a hand-held liquid dispenser means is positioned over microplate holder for a manual application of liquid. Although this device may be considerably less expensive than prior art automated devices, it is too slow and impractical for many laboratories. What is needed is relatively inexpensive automatic machine with simple mechanisms for rapidly filling a large volume of microplates without constant supervision.

SUMMARY OF THE INVENTION

The present invention provides an automated machine for filling a plurality of microplates. The automated machine includes at least one input stacking chamber for stacking empty microplates, at least one output stacking chamber for stacking filled microplates, and a microplate filling assembly disposed between the at least one input stacking chamber and the at least one output stacking chamber. The microplate filling assembly has a walking beam indexer, a lid lifter for lifting the lid off each microplate to permit the microplate to be filled, and after filling to replace the lid, and a fill mechanism in communication with a media source and positioned to fill the empty microplates after their lids have been lifted off. An automatic control unit is programmed to cause the walking beam indexer to move empty microplates from the at least one input stacking chamber, to cause the lid lifter to lift the lid off each microplate, to cause the fill mechanism to inject media from the media source into wells in the microplates, to cause the lid lifter to replace the lid after the media is injected, and to cause the walking beam indexer to move the microplates to the at least one output stacking chamber. In a preferred embodiment of the present invention, there are ten input stacking chambers and ten output stacking chambers and they are mounted on an input carousel and output carousel, respectively.

BRIEF DESCRIPTION OF THE DRAWINGS

FIGS. 2A–2D are a flowchart representing the programming for the programmable logic controller.

FIG. 3 shows a top view of a preferred embodiment of the present invention.

FIG. 4 shows a top view of the microplate filling assembly.

FIG. 5 shows a side view of a preferred embodiment of the present invention.

FIG. 6 shows a perspective view of the input chamber singulator.

FIG. 7 shows a detailed view of the input chamber singulator lifting input stack A.

FIGS. 10–39 show a sequence depicting the operation of a preferred embodiment of the present invention.

FIGS. 44–49 show a sequence depicting the operation of a preferred embodiment of the present invention.

FIG. 50 shows a perspective view of stack support pieces mounted to the output chamber.

FIG. 51 shows a side view of a stack support piece mounted to the output chamber.

DETAILED DESCRIPTION OF THE PREFERRED EMBODIMENTS

Figure 1C:
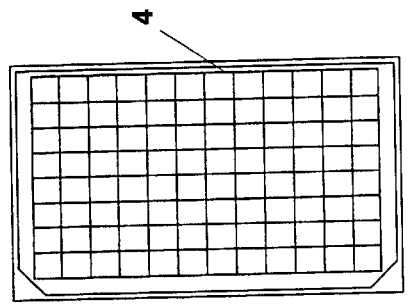
FIG. 1C shows a top view of a 96—well microplate base.

A detailed description of a first preferred embodiment of the present invention can be described by reference to FIGS. 1–39. A top view of a preferred embodiment of the present invention is seen in FIG. 3. FIG. 3 shows input carousel 3 and output carousel 5 connected by microplate filling assembly 6. During the operation of the present invention, empty microplates are stacked into input carousel 3, automatically filled with media via microplate filling assembly 6, and automatically restacked into output carousel 5.

As shown in FIG. 3, input carousel 3 has ten input chambers 15A–15J and output carousel 5 has ten output chambers 16A–16J. Each input chamber 15 and output chamber 16 is capable of receiving and holding a stack of twenty-four microplates. Therefore, a total of 240 empty microplates may be stacked in input carousel 3, automatically filled via microplate filling assembly 6, and automatically restacked into output carousel 5.

FIG. 4 shows a detailed top view of microplate filling assembly 6 with microplates located at positions α–ε along microplate filling assembly 6.

Sequence of Operation of a Preferred Embodiment

FIGS. 10–39 illustrate the sequence of operation of the first preferred embodiment of the present invention.

Figure 9:
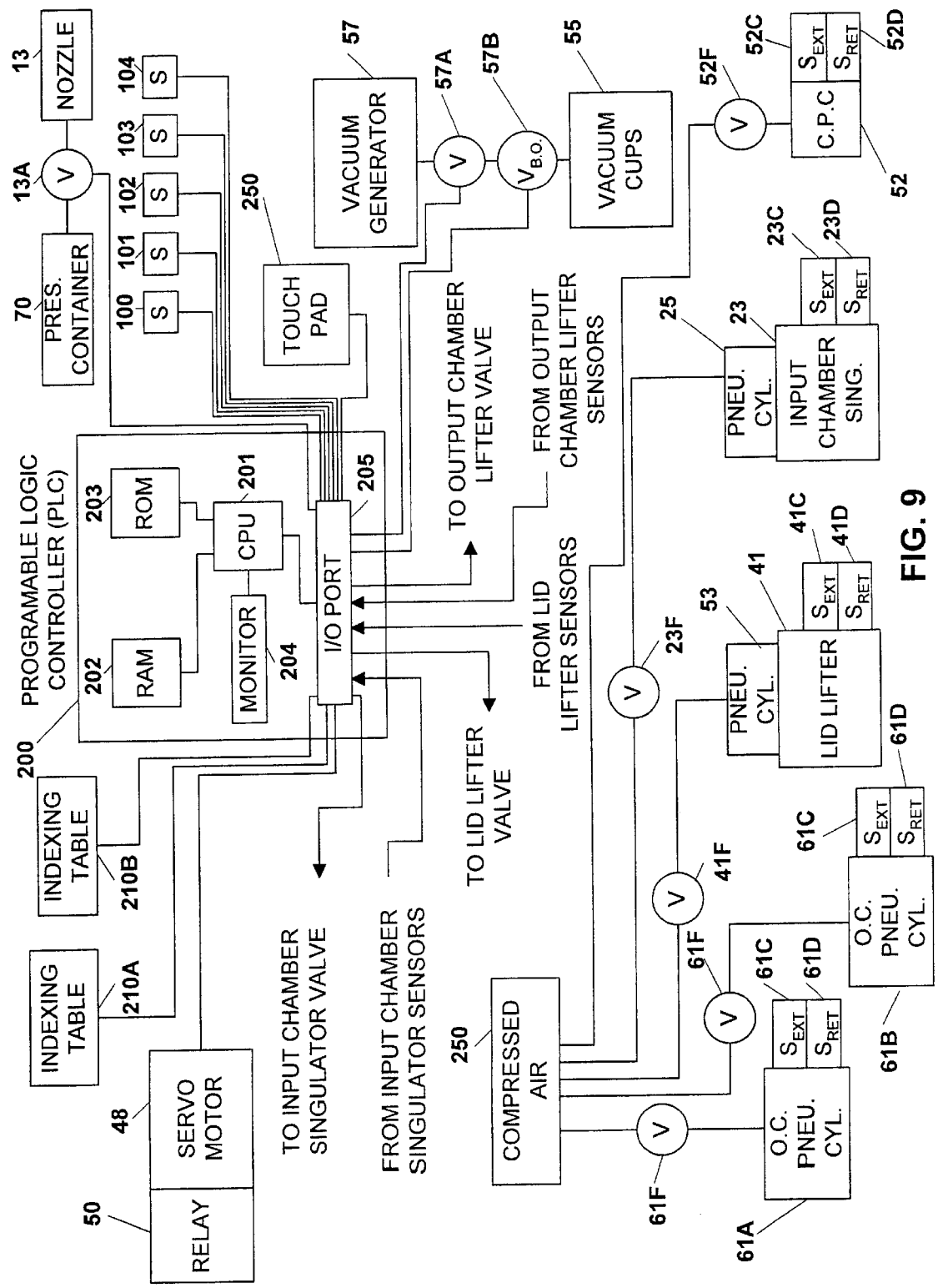
FIG. 9 shows a block diagram of the programmable logic controller other components of a preferred embodiment of the present invention.

In a preferred embodiment of the present invention, the operation of the components is controlled by programmable logic controller (PLC) 200, as shown in FIG. 9. FIGS. 2A–2E show a flowchart representing preferred programming of PLC 200 and corresponds with the sequence illustrated in FIGS. 10–34.

Figure 2A:
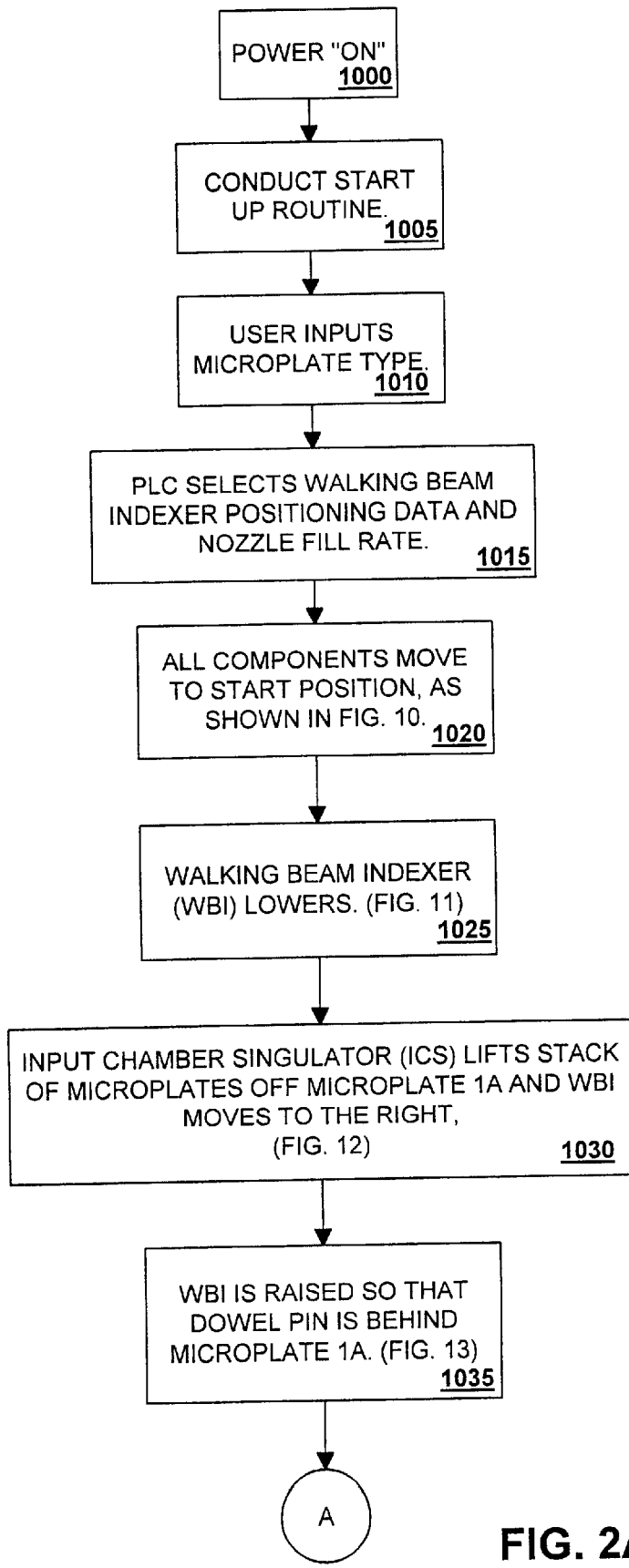
Figure 2B:
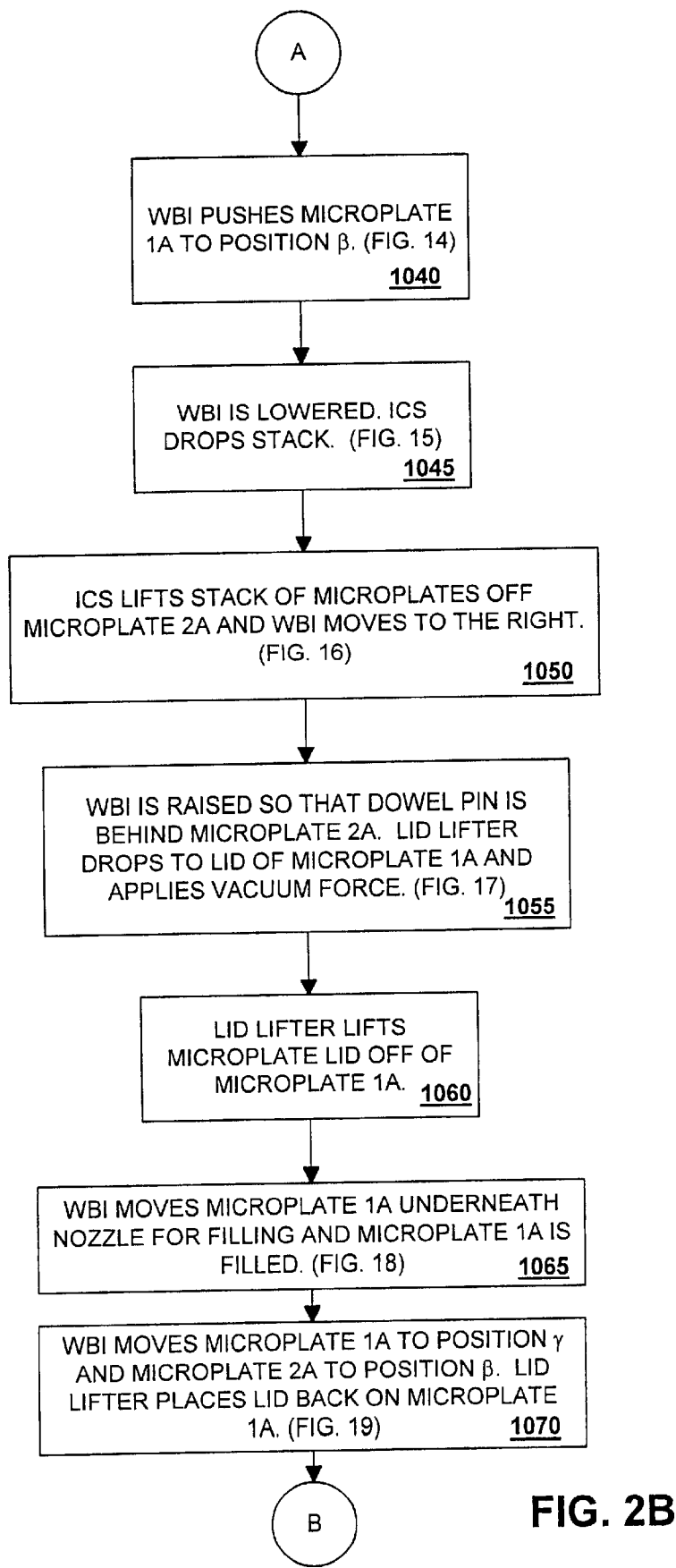
Figure 2C:
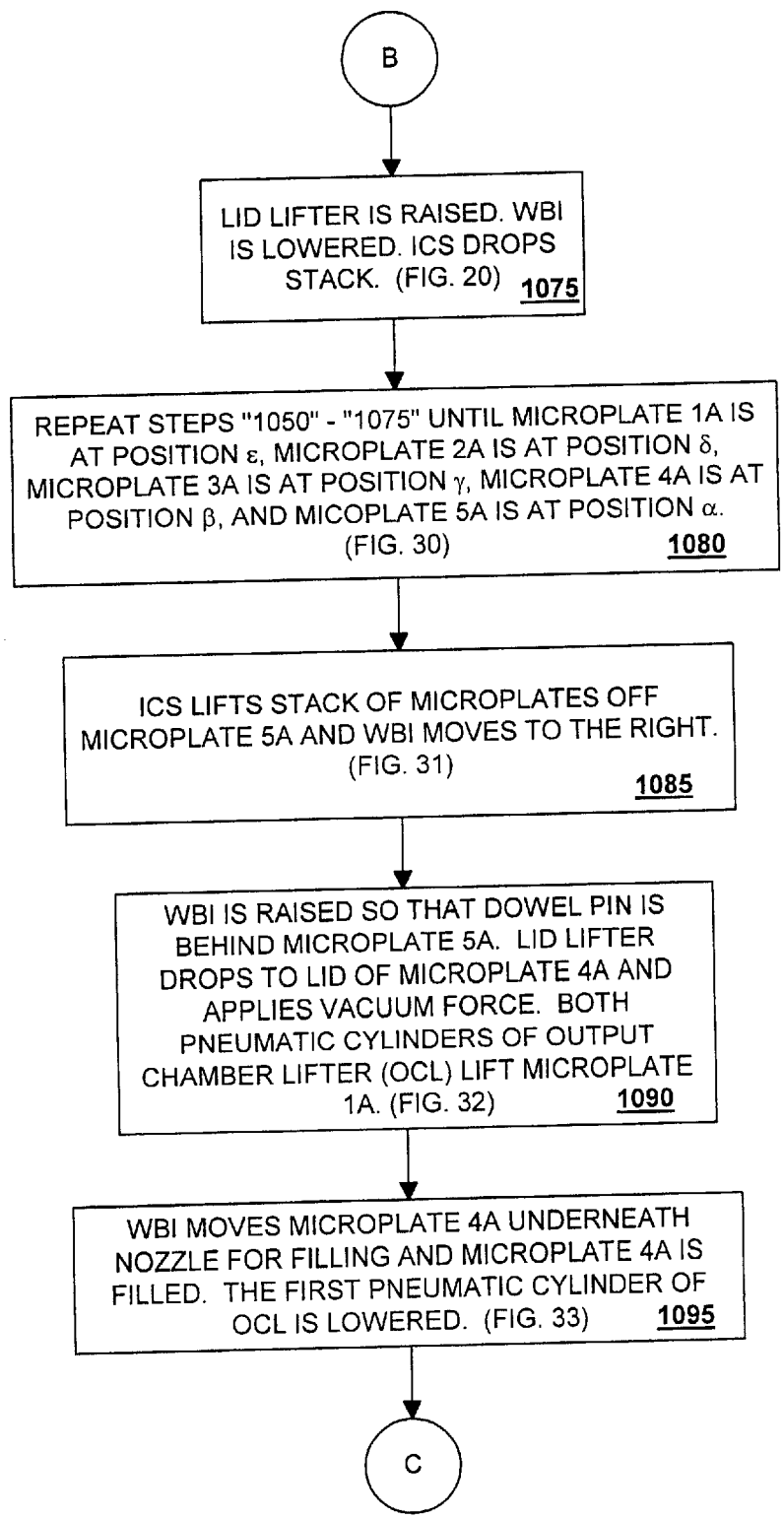

As shown in FIG. 2A, steps 1000–1005, after the user powers "on" the present invention, PLC 200 automatically conducts a start up routine. In this routine, PLC 200 checks all PLC 200 controlled components, homes all pneumatic devices and checks all sensors. If there are any errors (for example, jammed microplates or component malfunction), the user will be alerted via monitor 204 (FIG. 9).

As shown in FIG. 2A, step 1010, the user inputs the type of microplate that he wants to be filled (i.e., either a single-well, 96-well, or 384-well microplate). As shown in step 1015, because the nozzle type varies depending on the microplate selected, the user must install the correct nozzle. Depending upon the microplate selected by the user in the start up routine, PLC 200 selects walking beam indexer 7 positioning data and nozzle 13 fill rate.

All components move to their start position. FIG. 10 shows a stack of twenty-four empty microplates 1A–24A loaded into input chamber 15A. Microplate 1A is at the bottom at position α (FIG. 4) and microplate 2A is directly above microplate 1A. Microplate 24A is at the top of the stack. In FIG. 10 output stack A located inside output chamber 16A is empty with no microplates.

In FIG. 11, walking beam indexer 7 has lowered so that dowel pins 14 are below the horizontal plane formed by the top surface of beam 8.

In FIG. 12, input chamber singulator 23 has lifted input stack A2–A24 at microplate 2A. Microplate 1A is left at position α, as shown in FIG. 4. A detailed view of input chamber singulator 23 lifting input stack A is seen in FIG. 7. Tab singulator 33 lifts microplate 2A allowing a small gap to form between microplate 1A and 2A. Since input stack A2–A24 is confined on all sides by input chamber 15A, instead of tilting input stack A2–A24, lifting from the front edge lifts the entire stack vertically. Also as shown in FIG. 12, walking beam indexer 7 has moved to the right.

In FIG. 13, walking beam indexer 7 is raised so that dowel pin 14 is located directly behind microplate 1A.

Figure 14:
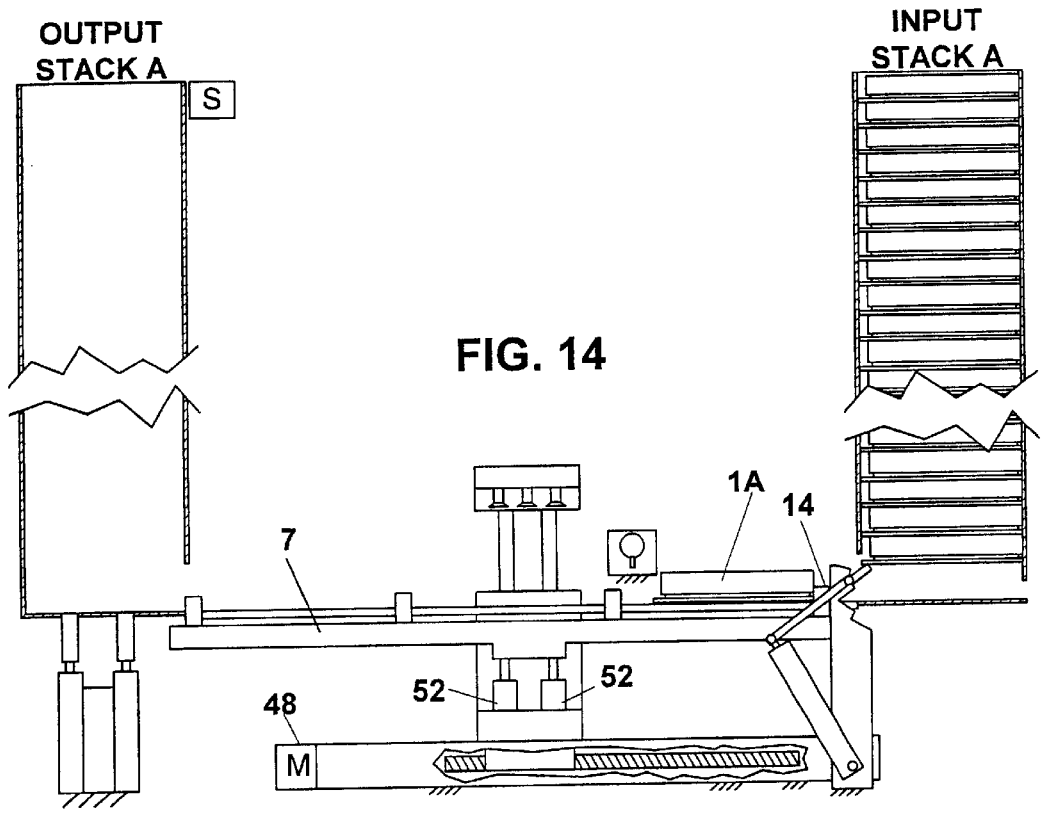

In FIG. 14, walking beam indexer 7 has moved to the left pushing microplate 1A to position β (see FIG. 4) from the bottom of the stack.

Figure 15:
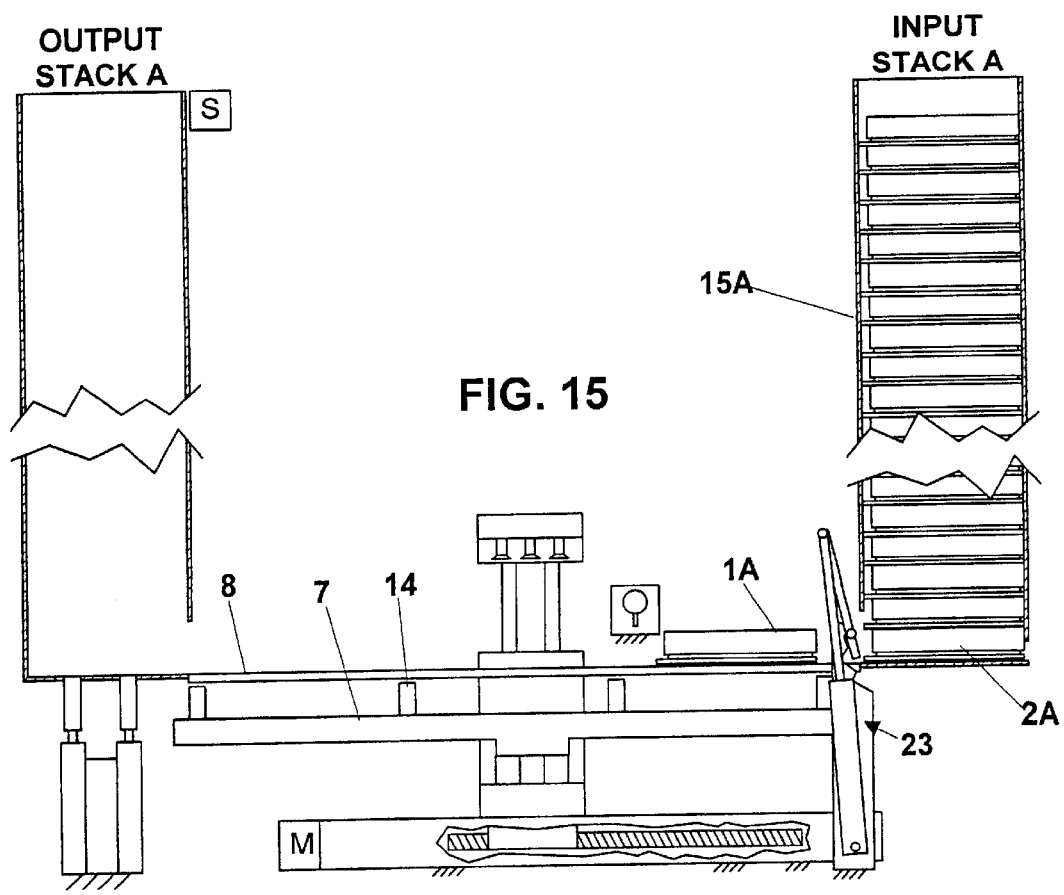

In FIG. 15, walking beam indexer 7 has been lowered so that dowel pins 14 are below the horizontal plane formed by the top surface of beam 8. Input chamber singulator 23 has dropped input stack A. Microplate 1A is at position p and microplate 2A is at position α.

In FIG. 16, walking beam indexer 7 has moved to the right. Input chamber singulator 23 has lifted input stack A3–A24, leaving behind microplate 2A at position α.

Figure 18:
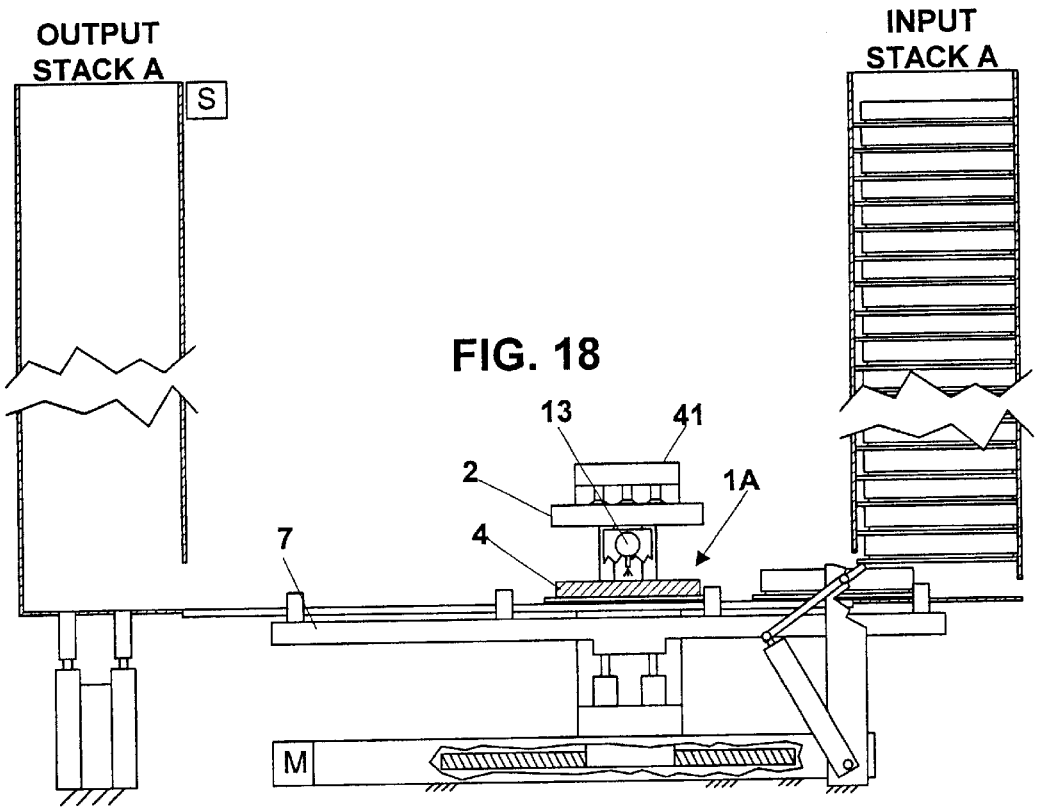

In FIG. 17, lid lifter 41 has dropped to the top of microplate lid 2 of microplate 1A, has grasped microplate lid 2 with a vacuum force and will lift microplate lid 2 prior to the display shown in FIG. 18. Walking beam indexer 7 is raised so that dowel pin 14 is located directly behind microplate 2A.

Figure 1B:
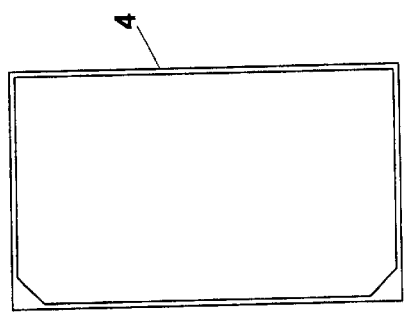
FIG. 1B shows a top view of a single-well microplate base.
Figure 1A:
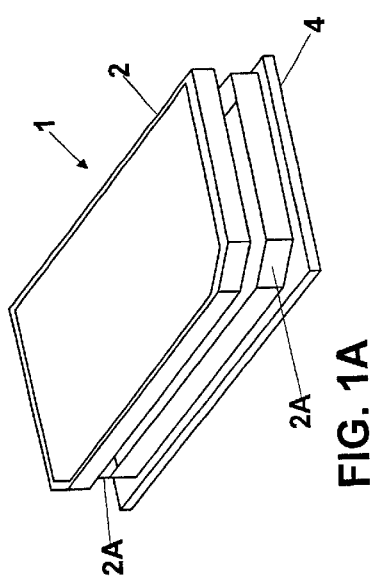
FIG. 1A shows a perspective view of a single-well microplate.
Figure 1D:
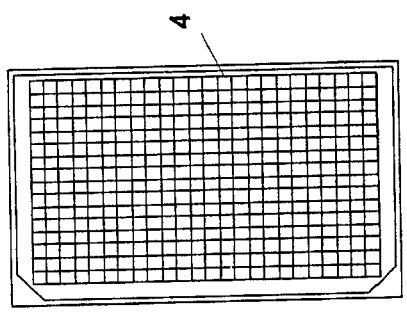
FIG. 1D shows a top view of a 384—well microplate base.

In FIG. 18, lid lifter 41 has lifted microplate lid 2 off of microplate 1A. Walking beam indexer 7 has moved microplate base 4 of microplate 1A to the left underneath nozzle 13. If single well plates are being used as shown in FIGS. 1A and 1B, walking beam indexer 7 will move microplate 1A to a center location to fill microplate 1A with media. If microplate 1A is a multi-welled microplate (for example, a 96 or 384-welled plate), walking beam indexer 7 will first move microplate 1A to so that the first row is underneath nozzle 13. After the first row is filled, walking beam indexer 7 will move microplate 1A to the left so that the second row is underneath nozzle 13 so that it can be filled. Walking beam indexer 7 will continue to move microplate 1A incrementally in this manner until all rows are filled. As shown in FIG. 18, microplate lid 2 is being held directly over microplate base 4 by lid lifter 41.

Figure 19:
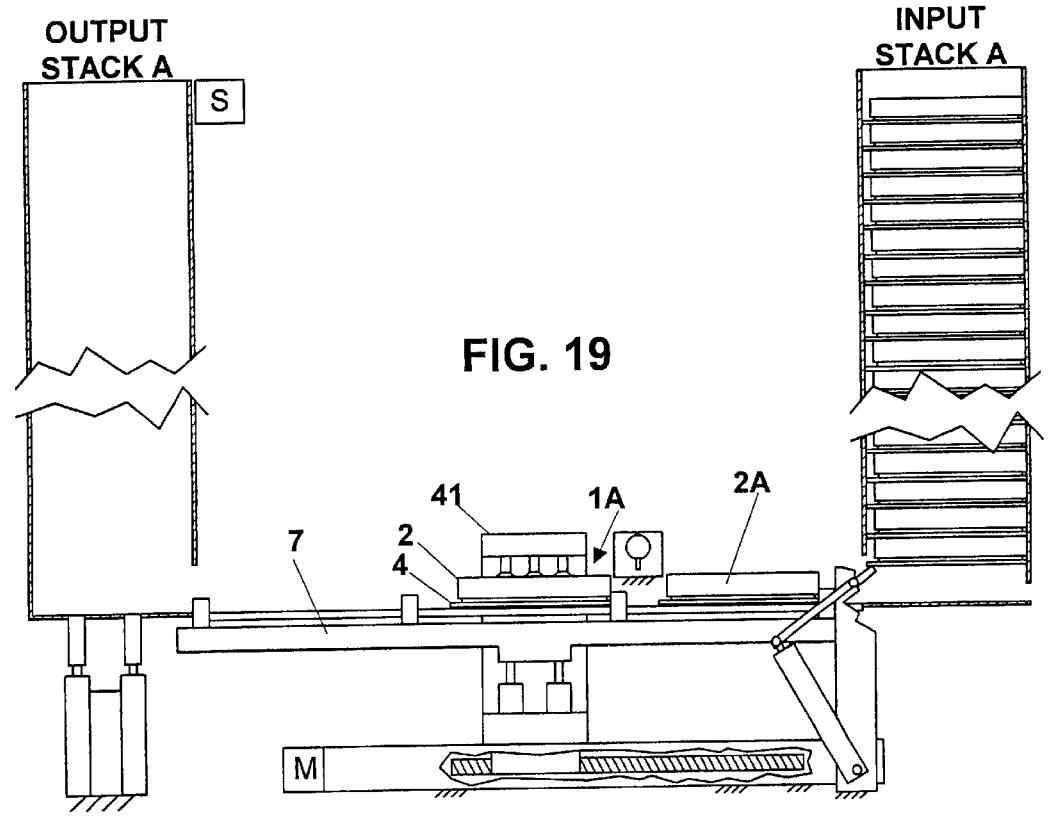

In FIG. 19, walking beam indexer 7 has moved further to the left. Lid lifter 41 has returned microplate lid 2 of microplate 1A to microplate base 4. Microplate 1A is at position γ (see FIG. 4) and microplate 2A is at position β. Microplate 1A is now filled with media 11.

In FIG. 20, input chamber singulator 23 has dropped input stack A. Lid lifter 41 has been raised. Microplate 1A is at position y (FIG. 4), microplate 2A is at position β, and microplate 3A is at position a. Walking beam indexer 7 has been lowered so that dowel pins 14 are below the horizontal plane formed by the top surface of beam 8.

In FIG. 21, walking beam indexer 7 has moved to the right. Input chamber singulator 23 has lifted input stack A4–A24, leaving behind microplate 3A at position α.

Figure 22:
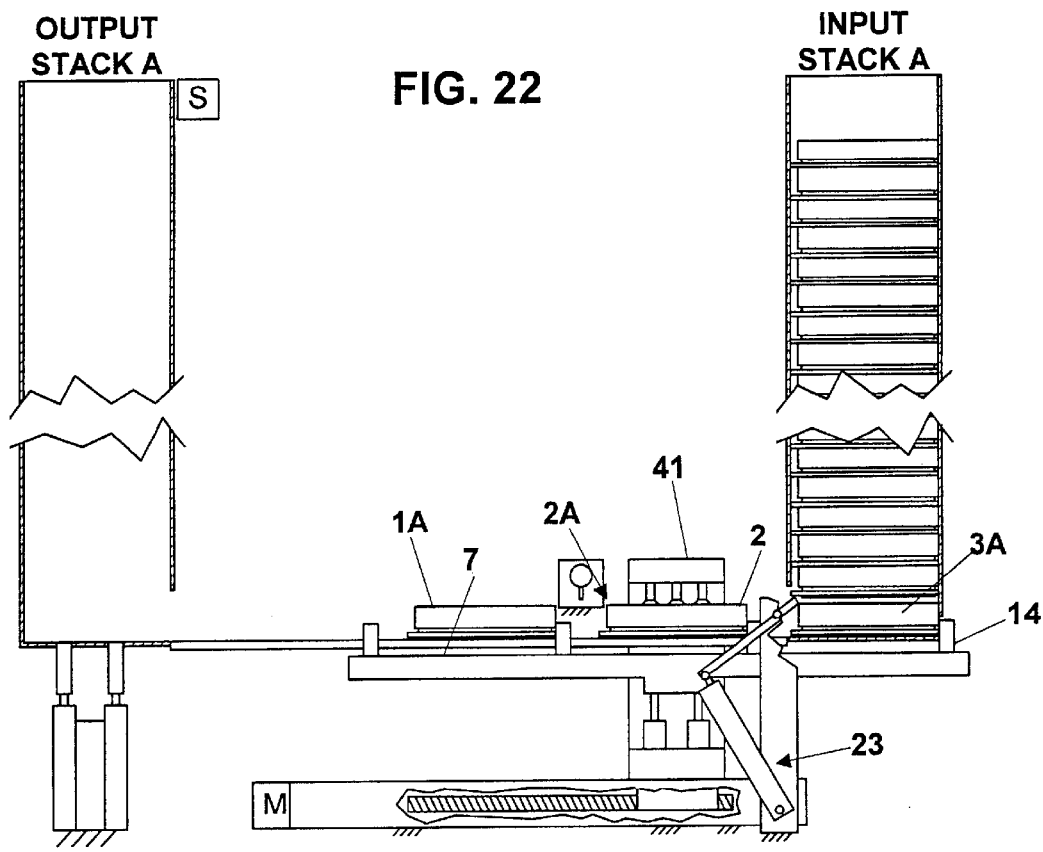
Figure 23:
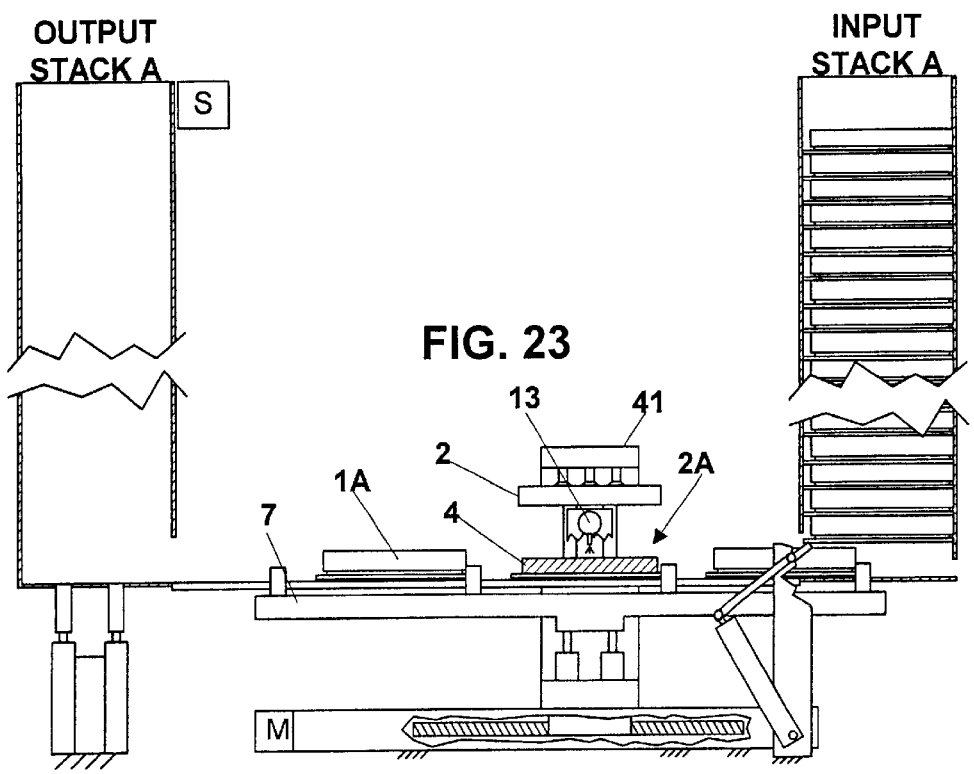

In FIG. 22, lid lifter 41 has dropped to the top of microplate lid 2 of microplate 2A, has grasped microplate lid 2 with a vacuum force and will lift microplate lid 2 prior to the display shown in FIG. 23. Walking beam indexer 7 is raised so that dowel pin 14 is located directly behind microplate 3A.

In FIG. 23, lid lifter 41 has lifted microplate lid 2 off of microplate 2A. Walking beam indexer 7 and lid lifter 41 have moved to the left. Microplate base 4 of microplate 2A is underneath nozzle 13 and is being filled with media 11. Microplate lid 2 is being held directly over microplate base 4 by lid lifter 41.

Figure 24:
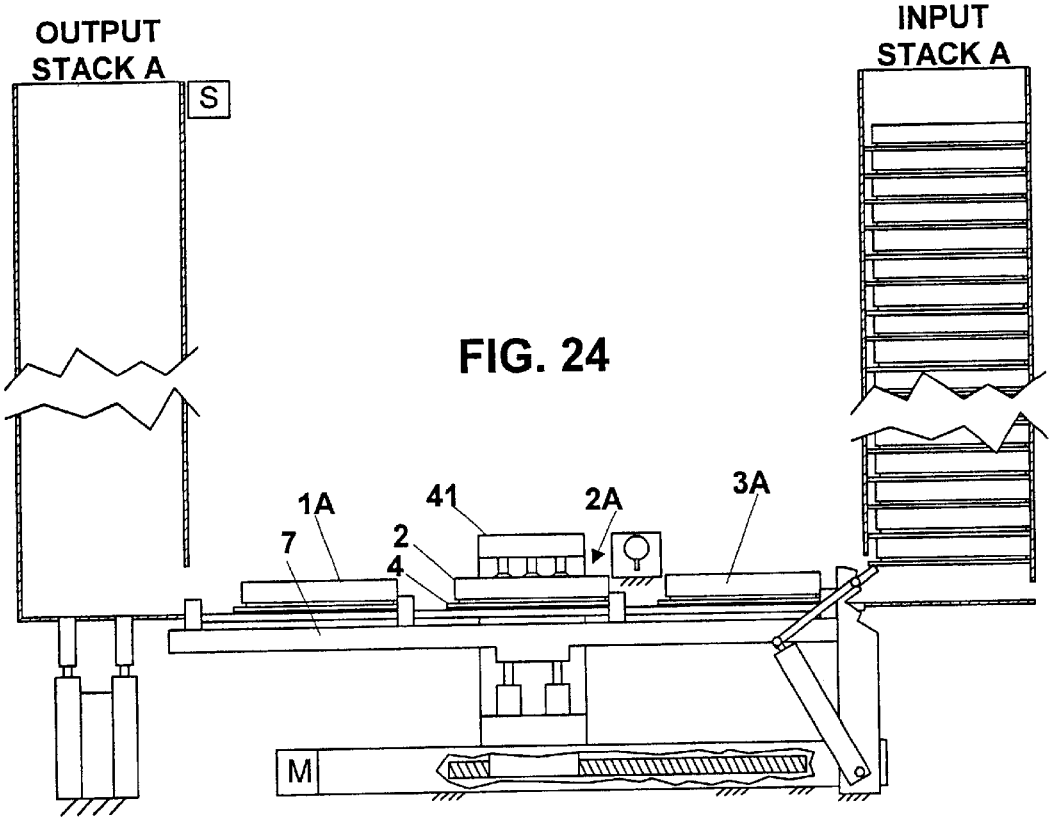

In FIG. 24, walking beam indexer 7 has moved further to the left. Lid lifter 41 has returned microplate lid 2 of microplate 2A to microplate base 4. Microplate 1A is at position δ, microplate 2A is at position γ, microplate 3A is at position β (FIG. 4). Microplate 2A is now filled with media 11.

Figure 25:
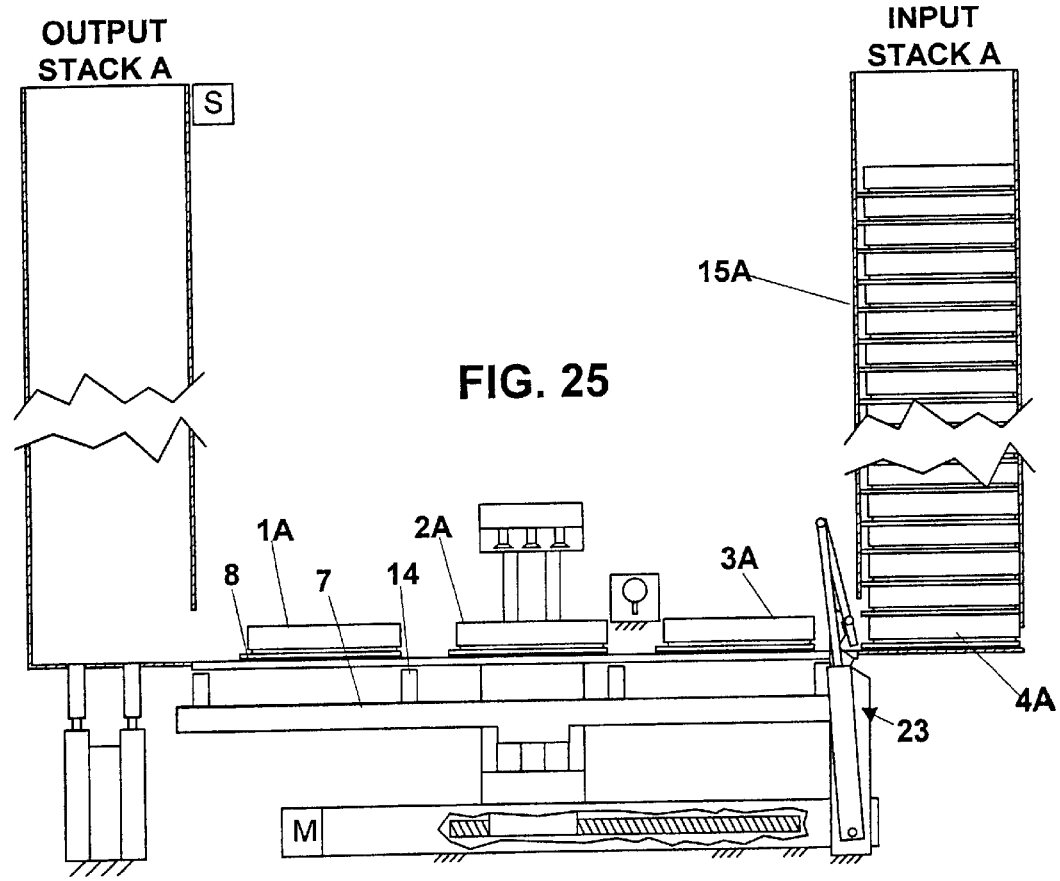

In FIG. 25, input chamber singulator 23 has dropped input stack A. Lid lifter 41 has been raised. Walking beam indexer 7 has been lowered so that dowel pins 14 are below the horizontal plane formed by the top surface of beam 8.

In FIG. 26, walking beam indexer 7 has moved to the right. Input chamber singulator 23 has lifted input stack A5–A24, leaving behind microplate 4A at position α.

In FIG. 27, lid lifter 41 has dropped to the top of microplate lid 2 of microplate 3A, has grasped microplate lid 2 with a vacuum force and will lift microplate lid 2 prior to the display shown in FIG. 28. Walking beam indexer 7 is raised so that dowel pin 14 is located directly behind microplate 4A.

In FIG. 28, lid lifter 41 has lifted microplate lid 2 off of microplate 3A. Walking beam indexer 7 and lid lifter 41 have moved to the left. Microplate base 4 of microplate 3A is underneath nozzle 13 and is being filled with media 11. Microplate lid 2 is being held directly over microplate base 4 by lid lifter 41. Microplate 1A is being moved inside of output chamber 16A.

In FIG. 29, walking beam indexer 7 has moved further to the left. Lid lifter 41 has returned microplate lid 2 of microplate 3A to microplate base 4. Microplate 1A is at position ε, microplate 2A is at position δ, microplate 3A is at position γ, and microplate 4A is at position β (FIG. 4). Microplate 3A has been filled with media 11.

Figure 30:
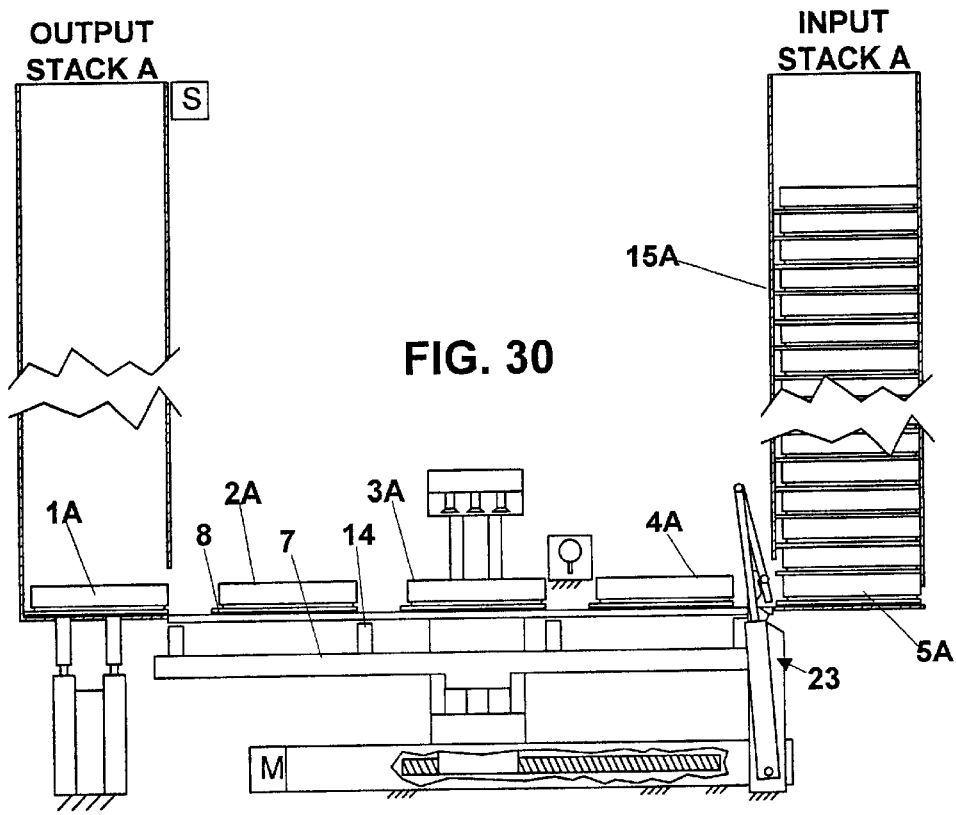

In FIG. 30, input chamber singulator 23 has dropped input stack A. Lid lifter 41 has been raised. Walking beam indexer 7 has been lowered so that dowel pins 14 are below the horizontal plane formed by the top surface of beam 8.

Figure 31:
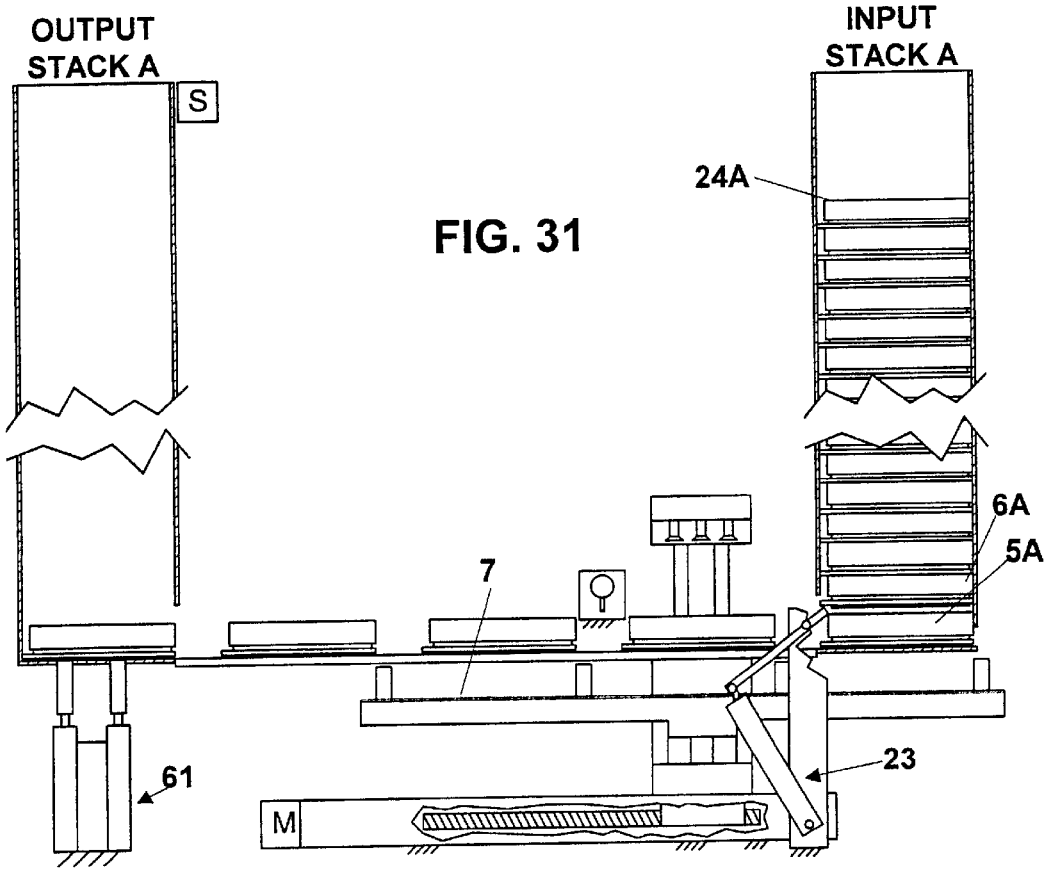

In FIG. 31, walking beam indexer 7 has moved to the right. Input chamber singulator 23 has lifted input stack A6–A24, leaving behind microplate 5A at position α.

In FIG. 32, lid lifter 41 has dropped to the top of microplate lid 2 of microplate 4A, has grasped microplate lid 2 with a vacuum force and will lift microplate lid 2 prior to the display shown in FIG. 33. Walking beam indexer 7 is raised so that dowel pin 14 is located directly behind microplate 5A. Output chamber lifter 61 has lifted microplate 1A to allow room for microplate 2A to be restacked from the bottom.

In FIG. 33, lid lifter 41 has lifted microplate lid 2 off of microplate 4A. Walking beam indexer 7 and lid lifter 41 have moved to the left. Microplate base 4 of microplate 4A is underneath nozzle 13 and is being filled with media 11. Microplate lid 2 is being held directly over microplate base 4 by lid lifter 41. Output chamber lifter cylinder 61A has dropped allowing room for microplate 2A to enter output chamber 16A. Microplate 1A is resting on output chamber lifter cylinder 61B and microplate 2A.

In FIG. 34, walking beam indexer 7 has moved further to the left. Lid lifter 41 has returned microplate lid 2 of microplate 4A to microplate base 4. Microplate 2A is at position ε, microplate 3A is at position δ, microplate 4A is at position γ, and microplate 5A is at position β (FIG. 4). Microplate 3A has been filled with media 11. Output chamber lifter cylinder 61B has dropped and microplate 1A is resting on microplate 2A inside output chamber 16A.

The sequence continues as described above until input stack A is empty, as shown in FIG. 35. FIG. 35 shows a stack of twenty-one filled microplates loaded into output chamber 16A. Microplate 1A is at the top of output stack A and microplate 2A is directly underneath microplate 1A. Microplate 21A is at the bottom of output stack A at position ε. Microplate 22A is at postion δ, microplate 23A is at position γ, and microplate 24A is at position β. Input stack A is empty with no microplates. Once sensor 100 (FIGS. 35 and 4) registers input stack A is empty, input carousel 3 (FIG. 3) rotates to so that input stack B is aligned with microplate filling assembly 6, as shown in FIG. 36.

FIG. 36 shows a stack of twenty-four empty microplates 1B–24B loaded into input chamber 15B. Microplate 1B is at the bottom at position α (FIG. 4) and microplate 2B is directly above microplate 1B. Microplate 24B is at the top of the stack. Microplate 21 A is at the bottom of output stack A at position ε. Microplate 22A is at postion δ, microplate 23A is at position γ, and microplate 24A is at position β. Lid lifter 41 has been raised. Walking beam indexer 7 has been lowered so that dowel pins 14 are below the horizontal plane formed by the top surface of beam 8.

The sequence continues until output stack A is completely filled, as shown in FIG. 37. FIG. 37 shows microplate 1A at the top of output stack A. Microplate 24A is at the bottom of output stack A at position β. Microplate 1B is at position δ, microplate 2B is at position γ, and microplate 3B is at position β. As soon as sensor 104 registers that microplate 1A is at the top of output stack A, output carousel 5 rotates so that output stack B inside output chamber 16B is aligned with microplate filling assembly 6, as shown in FIG. 38.

Figure 38:
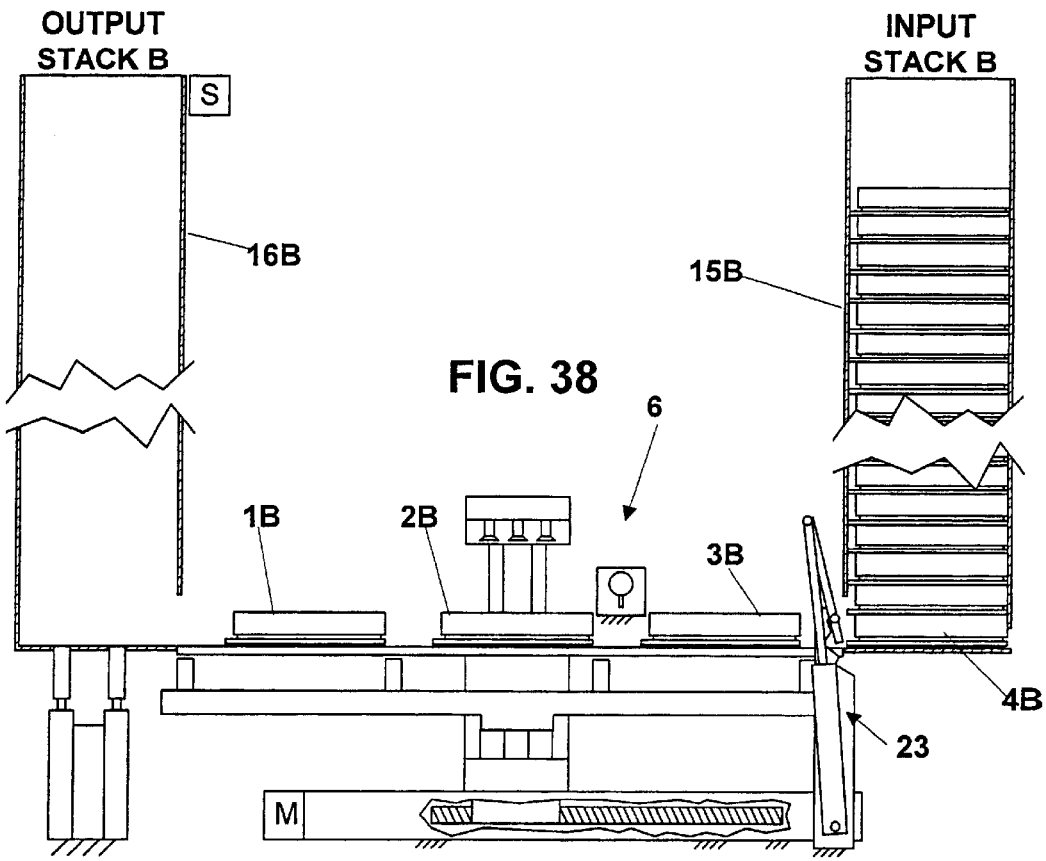

FIG. 38 shows microplate 1B at position 6, microplate 2B at position γ, and microplate 3B at position β. Input chamber singulator 23 has dropped input stack B and microplate 4B is at position α.

Figure 39:
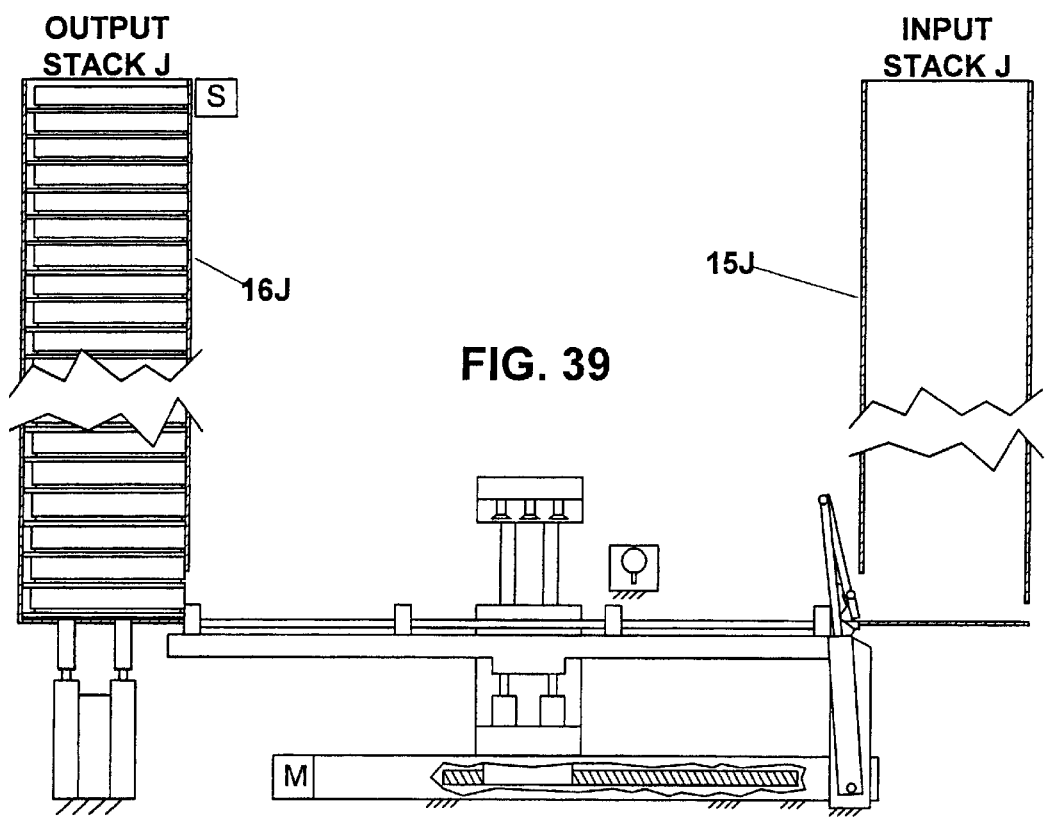

The above sequence continues until all the empty microplates that were originally in input carousel 3 have been filled and are restacked in output carousel 5. FIG. 39 shows an empty input chamber 15J and an output chamber 16J that has a full output stack J with filled microplates. If the operator desires, empty input chambers 15 from input carousel 3 can be reloaded with empty microplates while the machine is in operation, and it will continue to run.

Sensors 100 and 104 (FIGS. 4 and 37) and sensors 101, 102 and 103 (FIG. 4) continuously check for microplate presence. If there are no microplates in input carousel 3, this is recognized as an error and the process is stopped until more microplates are added to the system and the machine is restarted. The same is true for output carousel 5. If all 240 positions are filled in output carousel 5, the machine will recognize this as an error and will not continue until output chambers 16A–16J are emptied and the machine is restarted. If input carousel 3 is empty but sensors 101 though 103 report there are still microplates present in fill assembly 6 and sensor 104 reports there is still room in output carousel 5, the process will continue until all microplates are restacked in output carousel 5.

COMPONENTS OF A PREFERRED EMBODIMENT OF THE PRESENT INVENTION

Output and Input Carousels

In a preferred embodiment, input carousel 3 and output carousel 5 are fabricated from 0.060 thick 304 stainless steel. Base 17 (FIG. 3) has a diameter of approximately 16 inches. Input carousel 3 has 10 input chambers 15 mounted to base 17. Likewise, output carousel 5 has ten output chambers 16 mounted to base 17. Input chambers 15 and output chambers 16 are approximately 16.5 inches tall, have a depth of approximately 3.400 inches and are approximately 5.063 inches wide. Each input chamber 15 and output chamber 16 can hold twenty-four microplates 1. Chambers 15 and 16 are fabricated so that microplates 1 fit snuggly inside, but are able to slide freely up and down, as shown in FIG. 3. Chambers 15 and 16 are rigidly mounted to base 17 with mounting plates 19. As shown in FIG. 5, input carousel 3 and output carousel 5 are both rigidly mounted to position indexing tables 210A and 210B. Indexing tables 210A and 210B (part no. MT200S 10R) are manufactured by Kamo Seiko, Inc. and supplied by Land Sea, Inc. Indexing Tables 210A and 210B function to rotate input carousel 3 and output carousel 5 to ten different positions each so that each input chamber 15 and output chamber 16 can be directly aligned with walking beam indexer 7. As shown in FIG. 3, input chamber 15A and output chamber 16A are directly aligned with walking beam indexer 7.

Input Chamber Singulator

A detailed perspective view of a preferred embodiment of input chamber singulator 23 is shown in FIG. 6. Pneumatic cylinder 25 is pivotally mounted to bracket 27. Preferably, pneumatic cylinder 25 is a double acting/single rod pneumatic cylinder (part no. NCDJ2D04OOHB) manufactured by SMC, Inc. Link singulator 29 is pivotally mounted to pneumatic cylinder 25 and rigidly connected to rod singulator 31. Rod singulator 31 is mounted to singulator bearing blocks 35 and is free to rotate on plastic flange bearings 37. Tab singulators 33 are rigidly mounted to rod singulator 31. Bearing blocks 35 are rigidly mounted to supports 39, as shown in FIG. 6 and FIG. 10.

FIG. 12 shows pneumatic cylinder 25 in its retracted position with tab singulators 33 lifting microplate 2A. A detailed side view of tab singulator 33 lifting input stack A is shown in FIG. 7. Note that the triangular shape of tab singulators 33 (FIG. 6) corresponds to 45° recess 2A in microplates 1 (FIG. 1). Therefore, tab singulator 33 is able to lift input stack A without bumping into microplate lid 2, as shown in FIG. 7.

Walking Beam Indexer and Lid Lifter

Figure 8:
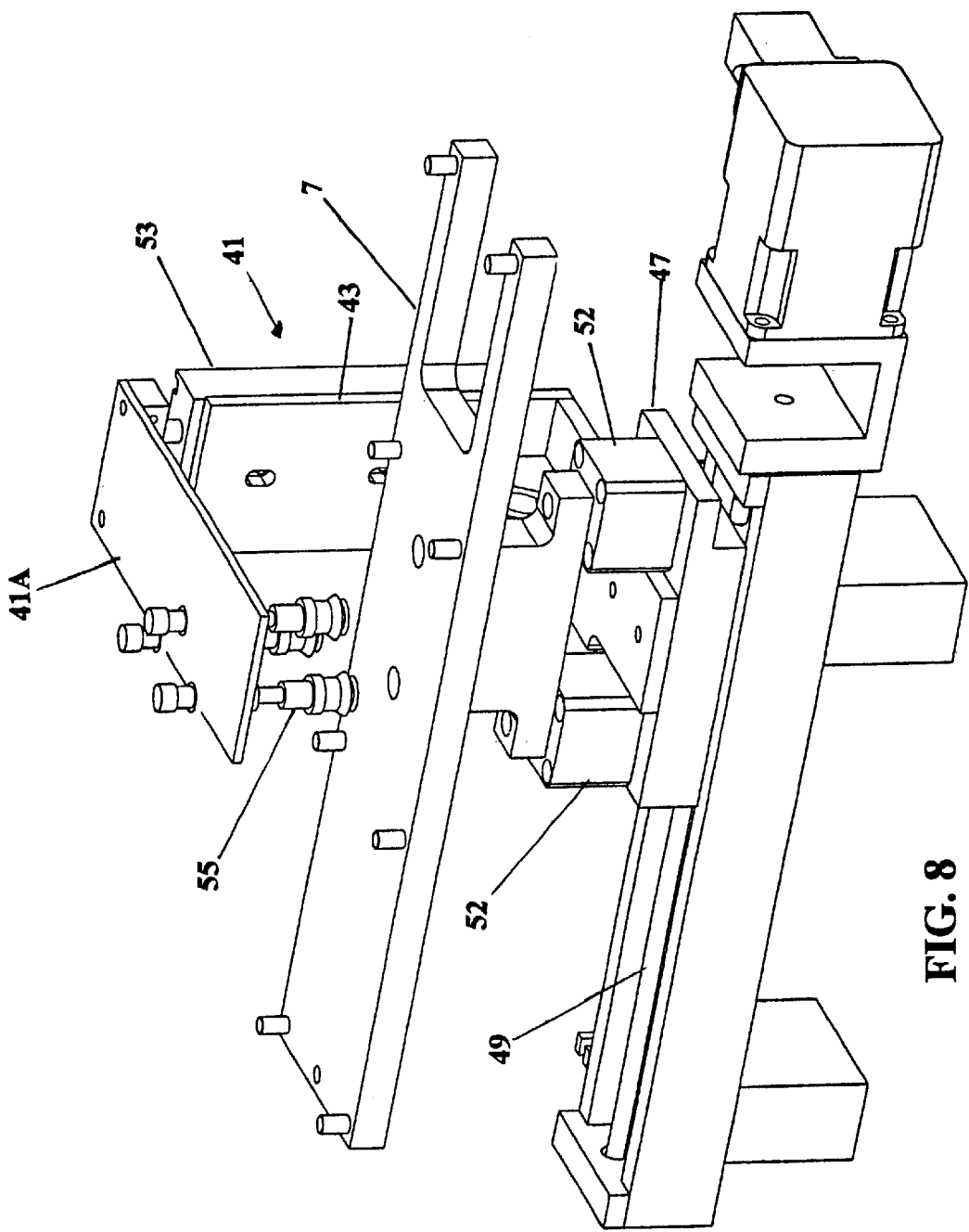
FIG. 8 shows a perspective view of the lid lifter and walking beam indexer.

FIG. 8 shows a perspective view of walking beam indexer 7 and lid lifter 41. Lid lifter 41 is rigidly mounted to lid lifter brackets 43. Lid Lifter brackets is rigidly connected to linear actuator threaded connector 47 (FIGS. 8 and 10). Linear actuator threaded connector is threaded onto lead screw 49 of linear actuator 45. Preferably, linear actuator 45 is an actuated linear motion system (part no. LC332001A-3001-P10) manufactured and available from Bearing Engineers, Inc. Lead screw 49 is actuated via servo motor 48. Preferably, servo motor 48 is an animatics motor (part no. SM2310) with amplifier and encoder all in one package Walking beam indexer 7 is mounted to compact pneumatic cylinders 52. When pneumatic cylinders 52 expand, walking beam indexer 7 is raised, as shown in FIG. 10. When pneumatic cylinders 52 retract, walking beam indexer 7 is lowered, as shown in FIG. 11. Preferably, compact cylinders are part number NCDQ2B20-10D-J79L manufactured by SMC and supplied by A & H Sales.

Pneumatic cylinder 53 is rigidly mounted to the back of indexer bracket 43, as shown in FIG. 8. Preferably, pneumatic cylinder 53 is a dual rod pneumatic cylinder (part no. CXSM-15-50-Y59B) manufactured by SMC, Inc. and available from A&H Sales. Lid lifter top 41A is rigidly connected to the top of pneumatic cylinder 53. Vacuum cups 55 extend downward from lid lifter top 41A. Vacuum lines connect vacuum cups 55 to vacuum generator 57, as shown in FIG. 9.

Linear actuator servo motor 48 (FIG. 10) rotates lead screw 49. As lead screw 49 rotates, linear actuator threaded connector 47 moves horizontally back and forth. Consequently, indexer bracket 43 moves horizontally back and forth. As it does so, it changes the horizontal location of both walking beam indexer 7 and lid lifter 41 together with an accuracy of plus or minus 0.0001 inches.

Output Chamber Lifter

As shown in FIG. 32, output chamber lifter 61 includes pneumatic cylinders 61A and 62A rigidly attached to bracket 62. Preferably, pneumatic cylinders 61A and 61B are dual rod pneumatic cylinders (part no. CXSM-15-50-Y59B) manufactured by SMC, Inc. and available from A&H Sales. As shown in FIGS. 32–34, output chamber lifter 61 functions to lift microplate 1A up while microplate 2A is inserted into output chamber 16A.

Programmable Logic Controller (PLC)

FIG. 9 depicts a block diagram of Programmable Logic Controller (PLC) 200 and other components of a preferred embodiment of the present invention. PLC 200 includes CPU 201 with associated memory (RAM 202, and ROM 203). Input/output port 205 connects PLC 200 with other components of the present invention. A user of the present invention can monitor the status of the operation of the present invention by way of monitor 204.

OPERATION OF A PREFERRED EMBODIMENT OF THE PRESENT INVENTION

Operating the Input Chamber Singulator

Input chamber singulator 23 can be in the drop position as shown in FIG. 11 or in the lift position as shown in FIG. 12. The drop position is to lower input stack A so that the bottommost microplate (microplate 1A) is at position α. The lift position is to lift input stack A (except for microplate 1A) off of microplate 1A so that microplate 1A can then be removed from the bottom.

In FIG. 10, two way solenoid valve 23F (FIG. 9) is in the open position and the rod in cylinder 25 of input singulator 23 is fully extended. To lift input stack A in input chamber 15A, PLC 200 sends an electric signal to return solenoid valve 23F to the closed position. This allows compressed air to enter cylinder 25 above its internal piston and the air below the piston is allowed to escape, causing the rod in pneumatic cylinder 25 to retract, as shown in FIG. 12. When the rod in pneumatic cylinder 25 is fully retracted, pneumatic retraction sensor 23D will send an electric signal to PLC 200 indicating the movement has been completed.

To lower input stack A in input chamber 15, PLC 200 sends an electric signal to open two way solenoid valve 23F (FIG. 9). This allows compressed air from compressed air source 250 to flow into pneumatic cylinder 25 below the internal piston and air above the piston is allowed to escape through an exhaust manifold, which causes the the rod in the cylinder to extend, as shown in FIG. 11. When the rod in pneumatic cylinder 25 is fully extended, pneumatic extension sensor 21C will send an electric signal to PLC 200 indicating the move has been completed.

Operating the Lid Lifter

Pneumatic cylinder 53 (FIG. 6) raises and lowers lid lifter 41. Lid lifter 41 is lowered so that the vacuum cups can rest on microplate lid 2, as shown in FIG. 17. Lid lifter 41 is raised so that it can lift microplate lid of microplate base 4 as shown in FIG. 18.

In FIG. 16, lid lifter 41 is in the fully extended position with two-way solenoid valve 41F open. To lower lid lifter 41, PLC 200 sends an electric signal to close two-way solenoid valve 41F. This allows compressed air below the internal piston inside pneumatic cylinder 53 to escape while allowing air to enter above the piston, causing the rod in pneumatic cylinder 53 to retract. This causes lid lifter 41 to drop, as shown in FIG. 17. When the rod in pneumatic cylinder 53 is fully retracted pneumatic retraction sensor 41D will send an electric signal to PLC 200 indicating the movement has been completed.

To raise lid lifter 41, PLC 200 sends an electric signal to open the two-way solenoid valve 41F (FIG. 9). This allows compressed air from compressed air source 250 to flow into pneumatic cylinder 53 below the piston and allows air above the piston to escape through the exhaust manifold, causing it to extend. This causes lid lifter 41 to raise, as shown in FIG. 18. When pneumatic cylinder 53 is fully extended pneumatic extension sensor 41C will send an electric signal to PLC 200 indicating the movement has been completed.

Operating the Output Chamber Lifter

Output chamber lifter 61 can be fully lowered (as shown in FIG. 31), filly raised (as shown in FIG. 32), or pneumatic cylinder 61A can be lowered while pneumatic cylinder 61B is raised (as shown in FIG. 33). The lowered position is to allow microplate 1A to slide into output chamber 16A and the raised position is to lift microplate 1A so that microplate 2A to enter output chamber 16A. The position where the rod in pneumatic cylinder 61A is lowered while the rod in pneumatic cylinder 61B is raised is to allow microplate 2A to provide support for microplate 1A while microplate 2A enters further into output chamber 16A.

The procedure to raise and lower output chamber lifter pneumatic cylinder 61A is identical to the procedure to raise and lower output chamber lifter pneumatic cylinder 61B. To raise output chamber lifter 61A, PLC 200 sends an electric signal to open two-way solenoid valve 61F. This allows compressed air from compressed air source 250 to flow into output chamber lifter pneumatic cylinder 61A below the internal piston and allows air above the piston to escape, which causes it to extend. When the rod in output chamber lifter pneumatic cylinder 61A is fully extended, pneumatic extension sensor 61C will send an electric signal to PLC 200 indicating the movement has been completed.

To lower output chamber lifter 61, PLC 200 sends an electric signal to close two-way solenoid valve 61F. This allows compressed air to enter output chamber lifter pneumatic cylinder 61A above the piston and allows the air below the piston to escape, causing the rod in output chamber lifter pneumatic cylinder 61A to retract. When the rod in output chamber lifter pneumatic cylinder 61A is fully retracted pneumatic retraction sensor 61D will send an electric signal to PLC 200 indicating the movement has been competed.

Raising and Lowering the Walking Beam Indexer

Walking beam indexer 7 is attached to compact pneumatic cylinders 52, as shown in FIG. 14. Walking beam indexer 7 can be raised (as shown in FIG. 14), or lowered (as shown in FIG. 15). Walking beam indexer 7 is raised in order to permit dowel pins 14 to push microplate 1A, as shown in FIG. 14. Walking beam indexer 7 is lowered so that as it moves from left to right, dowel pins 14 do not contact microplate 1A, as shown in FIGS. 15–16.

To raise the rod in compact pneumatic cylinder 52, PLC 200 sends an electric signal to open two-way solenoid valve 52F. This allows compressed air from compressed air source 250 to flow into compact pneumatic cylinder 52 below the internal piston and allows air above the piston to escape, which causes it to extend. When the rod in compact pneumatic cylinder 52 is fully extended, pneumatic extension sensor 52C will send an electric signal to PLC 200 indicating the movement has been completed.

To lower the rod in compact pneumatic cylinder 52, PLC 200 sends an electric signal to close two-way solenoid valve 52F. This allows compressed air to enter compact pneumatic cylinder 52 above the piston and allows the air below the piston to escape, causing the rod in compact pneumatic cylinder 52 to retract. When the rod in compact pneumatic cylinder 52 is fully retracted pneumatic retraction sensor 52D will send an electric signal to PLC 200 indicating the movement has been competed.

Error Checks

A preferred embodiment of the present invention has a variety of sensors that PLC 200 utilizes to conduct error checks. As shown in FIG. 4, sensor 100 is located beneath position $\alpha$ to verify a microplate is present at position $\alpha$. Likewise sensor 101 verifies microplate placement at position $\beta$, sensor 102 verifies microplate placement at position $\gamma$, sensor 103 verifies microplate placement at position $\delta$, and sensor 104 verifies microplate placement at the top of output chamber 16A, as shown in FIG. 10. Sensors 100 and 104 are photoelectric switches (part no. EQ-22-PN-J) supplied by Clayton Controls, and manufactured by SUNX. These sensors work by emitting a beam of light and switch "on" when the beam is blocked at a certain distance from the emitter. Sensors 101, 102, 103 are also photoelectric sensors (part number EX-14A-PN Manufactured by SUNX and supplied by Clayton Controls).

As shown in FIG. 9, each pneumatic component (input chamber singulator 23, lid lifter 41, output chamber lifter pneumatic cylinders 61A and 61B, and compact pneumatic cylinders 52) has two sensors: one that transmits an electrical signal when the component is fully extended (pneumatic extension sensors 61C, 41C, 23C, and 52C) and another sensor when it is fully retracted (pneumatic retraction sensors 61D, 41D, 23D, and 52D).

Linear actuator servo motor 48 includes a motor relay 50. If linear actuator servo motor 48 is jammed or malfunctioning, motor relay 50 will report an error to PLC 200 which will be displayed on monitor 204.

In a preferred embodiment of the present invention, PLC 200 is programmed to check its sensors continuously. It will check to verify that the microplates have correctly been moved to their appropriate positions, that linear actuator servo motor 48 is not jammed or malfunctioning, and that the pneumatic components have correctly extended or retracted.

In a preferred embodiment of the present invention, PLC 200 is Ethernet compatible and will allow the invention to be monitored for errors and throughput from another computer.

Performance

Applicants have built and tested a prototype model of the preferred embodiment of the present invention. During a dry run (i.e., not actually filling microplates with media), Applicants observed that the prototype model successfully moved six hundred microplates from input carousel 3 to output carousel 5 in one hour. This rate for moving microplates greatly exceeds that of the closest prior art. It should be noted that when filling microplates, the performance rate will vary depending on the type of microplate (i.e. single-well or multi-well) and on the type of media (i.e., Agar or liquid).

Figure 41:
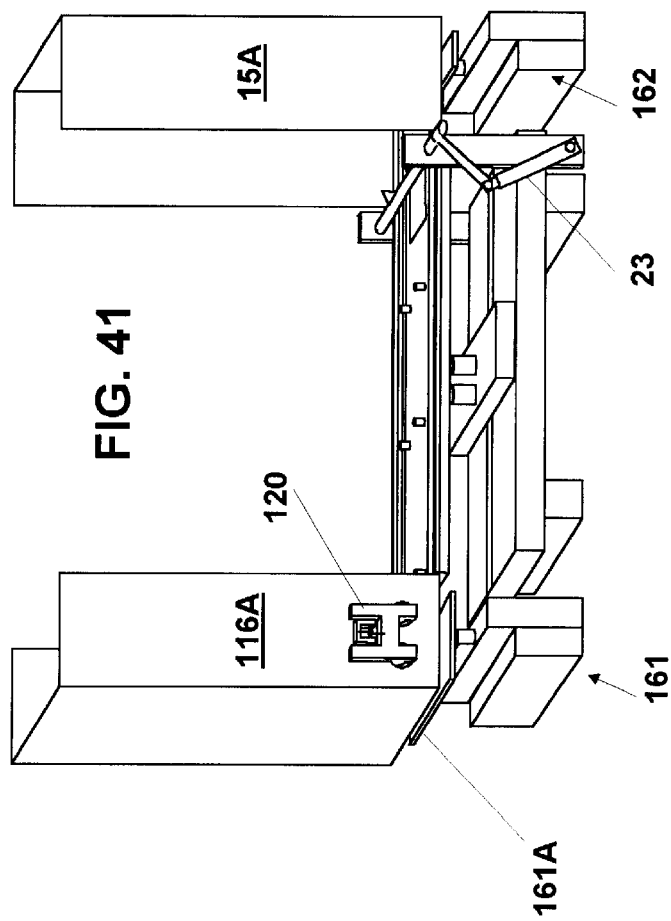
FIG. 41 shows a perspective view of some components of another preferred embodiment of the present invention.
Figure 40:
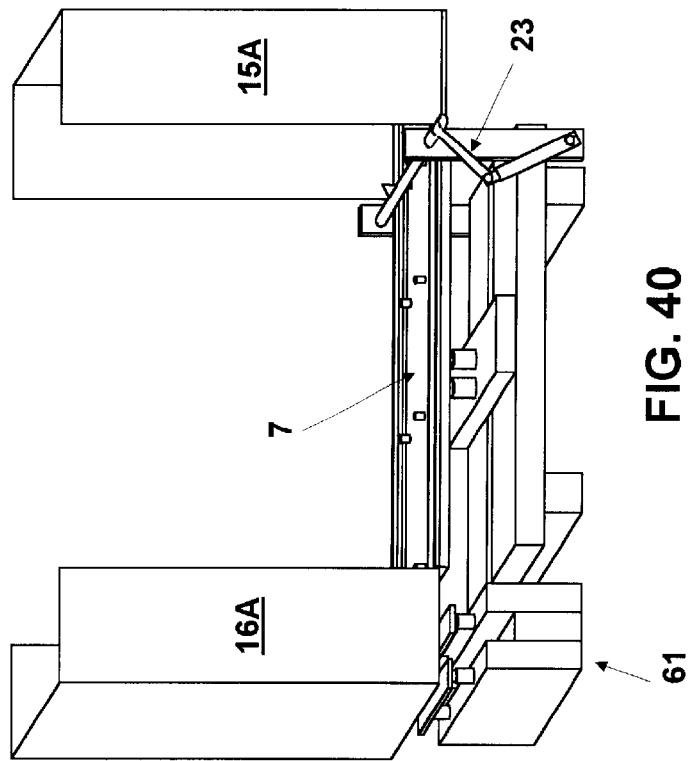
FIG. 40 shows a perspective view of some components of a preferred embodiment of the present invention.
Figure 42:
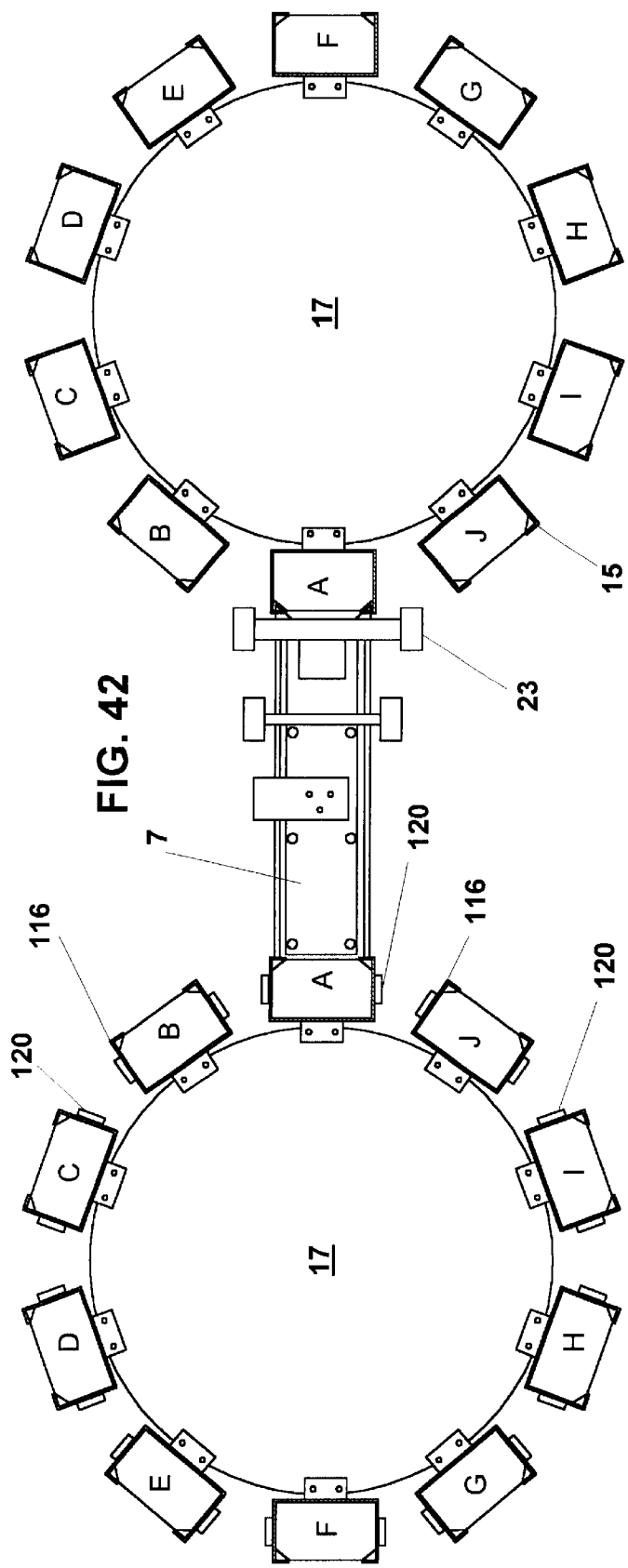
FIG. 42 shows a top view of a preferred embodiment of the present invention.

Other Preferred Embodiment with Improved Microplate Stack Handling FIG. 40 shows a perspective view of input chamber 15A, output chamber 16A, walking beam indexer 7, input chamber singulator 23, and output chamber lifter 61. The preferred embodiment shown in FIG. 40 was explained in detail in the sequence shown in FIGS. 10–39. FIG. 42 shows a top view of another preferred embodiment of the present invention with improved microplate stack handling. FIG. 41 shows some major components of the preferred embodiment depicted in FIG. 42. Output chamber 116A has stack support piece 120 mounted to both of its sides. Pneumatic output chamber lifter 161 is located directly underneath output chamber 116A and pneumatic input chamber lifter 162 is located directly underneath input chamber 15A.

DETAILED DESCRIPTION OF THE PREFERRED EMBODIMENT WITH IMPROVED MICROPLATE STACK HANDLING

Input Chamber with Input Chamber Lifter

As shown in FIG. 41, this preferred embodiment of the present invention includes input chamber lifter 162. Input chamber lifter 162 was added in order to help prevent tipping of the input stack after being lifted by input chamber singulator 23. A sequence illustrating the operation of pneumatic input chamber lifter 162 is seen by reference to FIGS. 44–49.

FIG. 44 shows a stack of twenty-four empty microplates 1A–24A loaded into input chamber 15A. Microplate 1A is at the bottom at position α (FIG. 4) and microplate 2A is directly above microplate 1A. Microplate 24A is at the top of the stack. In FIG. 44 output stack A located inside output chamber 116A is empty with no microplates.

In FIG. 45, walking beam indexer 7 has lowered so that dowel pins 14 are below the horizontal plane formed by the top surface of beam 8.

Figure 43:
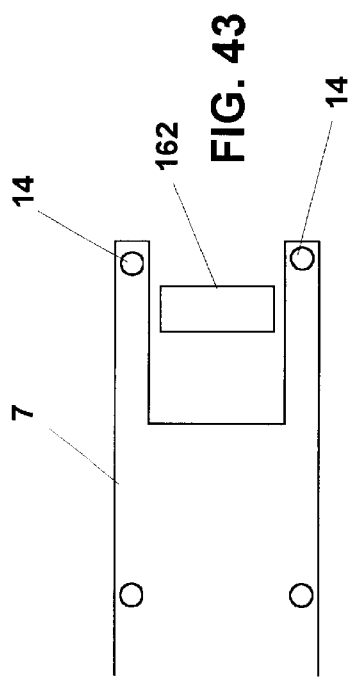
FIG. 43 shows a top view of the walking beam indexer and the input chamber lifter.

In FIG. 46, input chamber singulator 23 has lifted input stack A2–A24 at microplate 2A. Microplate 1A is left at position α, as shown in FIG. 4. Also as shown in FIG. 12, walking beam indexer 7 has moved to the right. As shown in FIG. 43, walking beam indexer 7 is fabricated so that it does not contact input chamber lifter 162 when it is moved to the right.

In FIG. 47, walking beam indexer 7 is raised so that dowel pin 14 is located directly behind microplate 1A.

Figure 48:
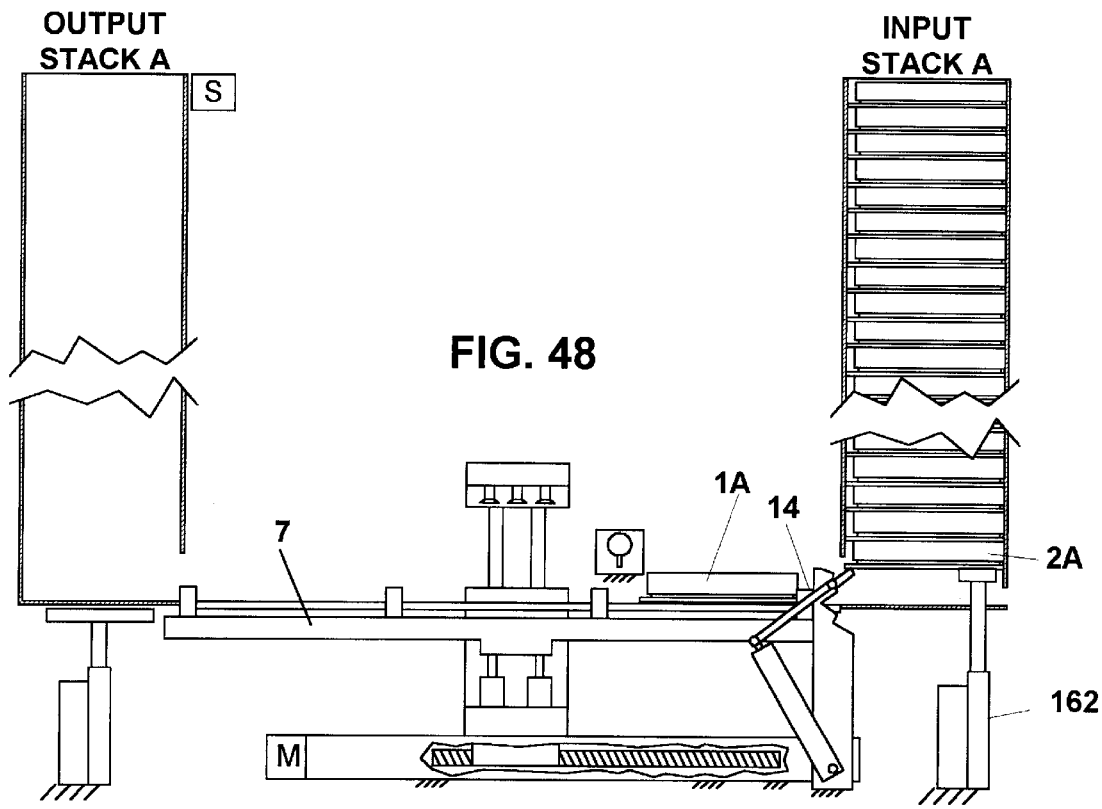

In FIG. 48, walking beam indexer 7 has moved to the left pushing microplate 1A to position β (see FIG. 4) from the bottom of the stack. As soon as microplate 1A is clear, input chamber lifter 162 extends to support input stack A2–A24. This helps prevent tipping of input stack A2–A24.

Figure 49:
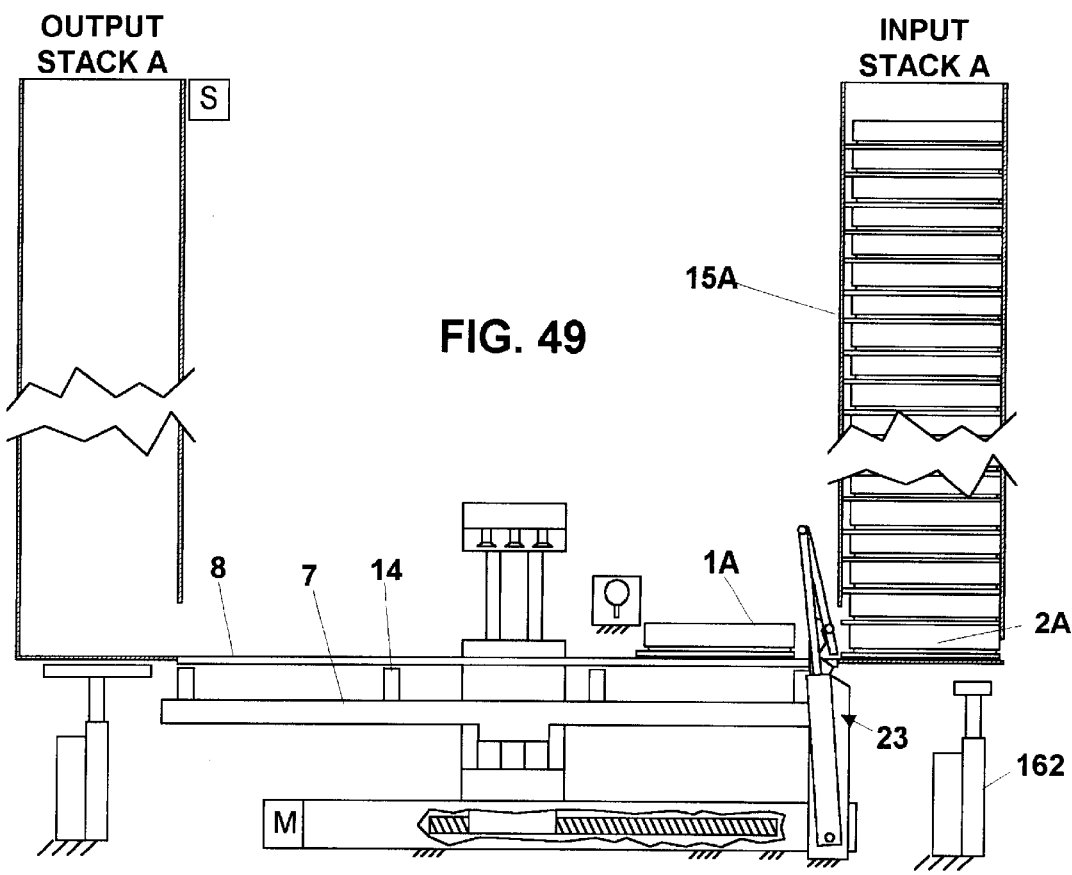

In FIG. 49, walking beam indexer 7 has been lowered so that dowel pins 14 are below the horizontal plane formed by the top surface of beam 8. Input chamber singulator 23 and input chamber lifter 162 have dropped input stack A. Microplate 1A is at position β and microplate 2A is at position α.

In a fashion similar to that described by reference to FIGS. 44–49, input chamber lifter 162 continues to operate in conjunction with input chamber singulator 23 to raise and lower the input stack in a manner to prevent tilting of the input stack.

Output Chamber with Stack Support Pieces

As shown in FIG. 42, output chambers 116A–116J each have two stack support pieces 120 mounted to their sides. FIG. 41 shows a perspective view of output chamber 116A with stack support piece 120 mounted to its side. Output chamber lifter 161 is directly under output chamber 116A. As shown in FIG. 41, output chamber lifter 161 has a single large lifting pad 161A. Single large lifting pad 161A provides a more stable support for the output stack than does the two lifting pad output chamber lifter 61 depicted in FIG. 40.

FIG. 50 shows a detailed perspective view of stack support piece 120 mounted to output chamber 116A and FIG. 51 shows a detailed side view of stack support piece 120 mounted to output chamber 116A. Mount 130 is rigidly attached to output chamber 116A. Axis 131 extends through mount 130 and stack support piece 120. Torsion spring 132 is wound around axis 131 and applies a force to mount 130 and stack support piece 120. This force tends to rotate stack support piece 120 in a counter-clockwise direction (FIG. 51) so that tapered support end 134 extends through hole 133 until stack support piece 120 is abutted by output chamber 116A.

A sequence illustrating the operation of output chamber 116A with stack support pieces 120 is seen by reference to FIGS. 52–55.

Figure 52:
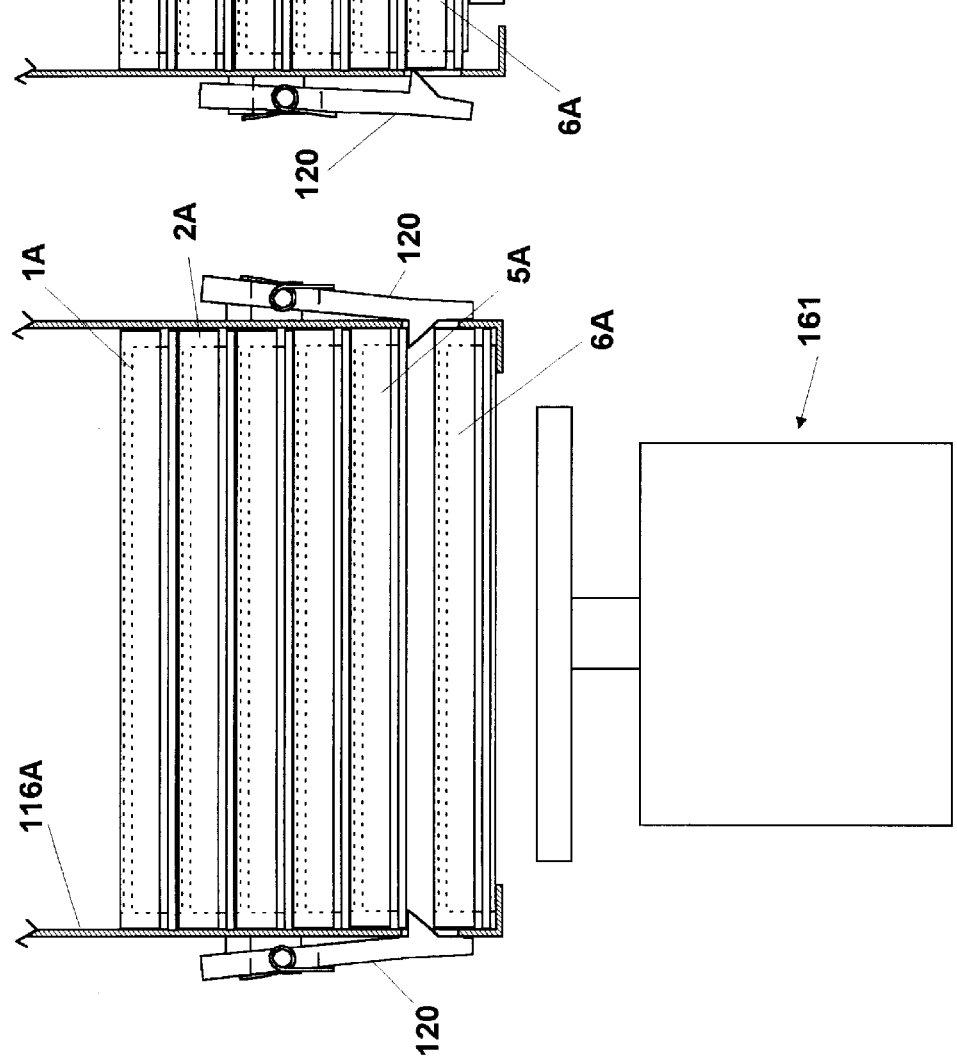

In FIG. 52, output stack A1–A6 is in output chamber 116A. Microplate 6A is at the bottom of the output stack a position ε (FIG. 4). Microplate 5A is above microplate 6A and is resting on stack support pieces 120.

Figure 53:
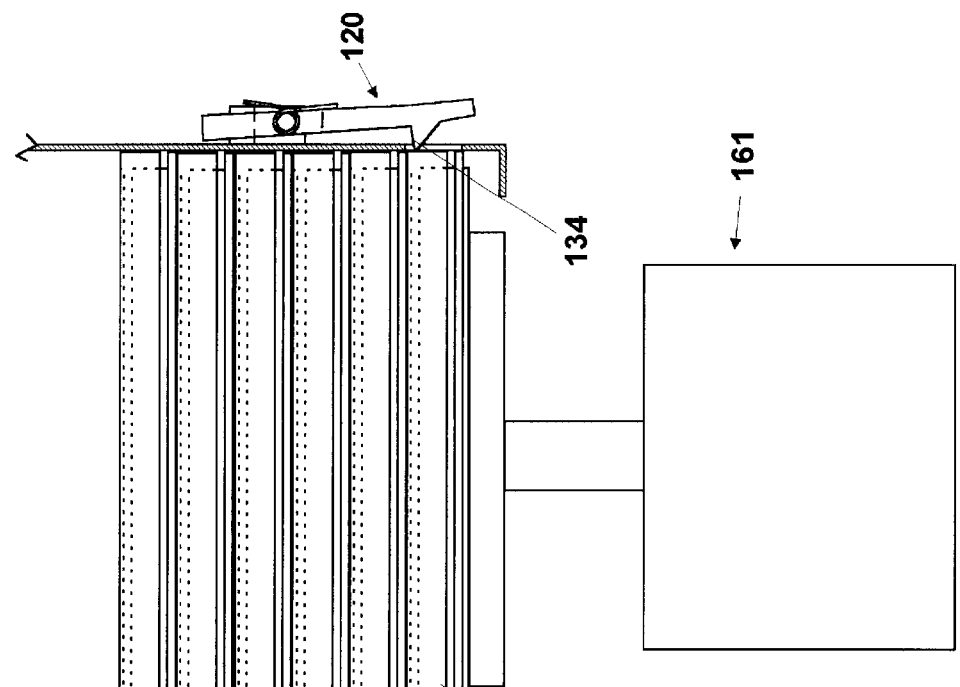
FIGS. 52–55 show a sequence depicting the operation of a preferred embodiment of the present invention.

In FIG. 53, output chamber lifter 161 is lifting output stack A1–A6 by pressing upward on microplate 6A. Tapered support end 134 of stack support piece 120 allows the upward movement of microplate 6A. As shown in FIG. 41, output chamber lifter 161 has a single large lifting pad 161A. Single large lifting pad 161A provides a more stable support for the output stack than does the two lifting pad output chamber lifter 61 depicted in FIG. 40.

Figure 54:
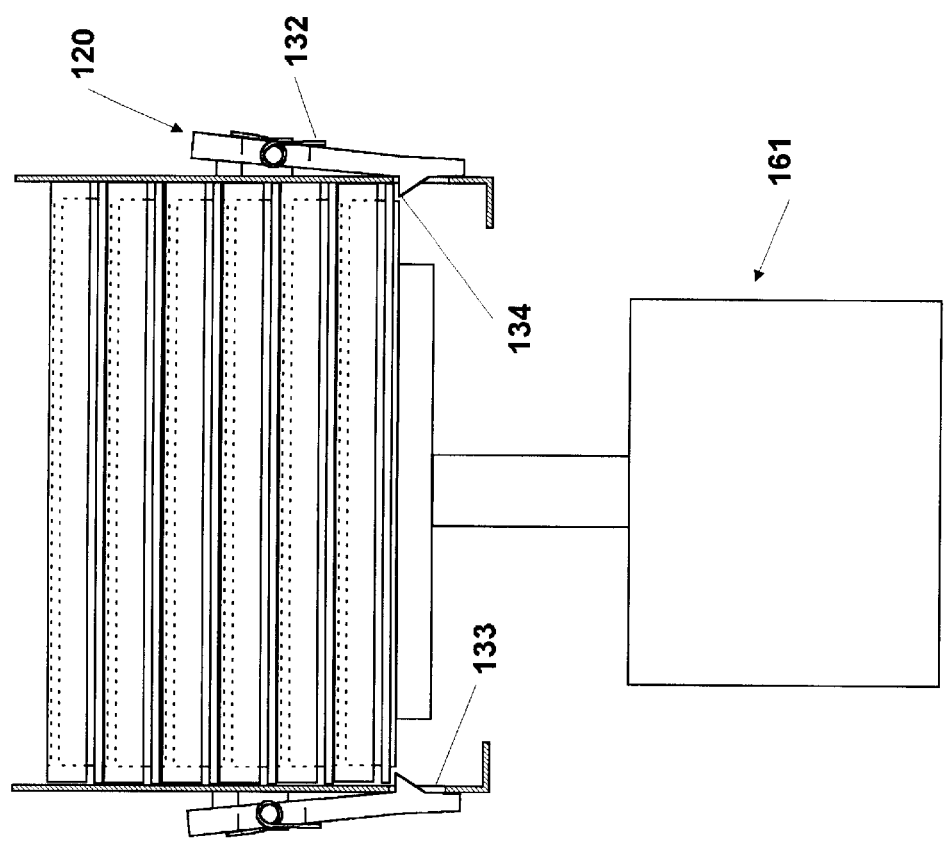

In FIG. 54, output chamber lifter 161 has lifted microplate 6A beyond tapered support ends 134. The force applied by torsion spring 132 against stack support piece 120 then moves tapered support end back through holes 133.

Figure 55:
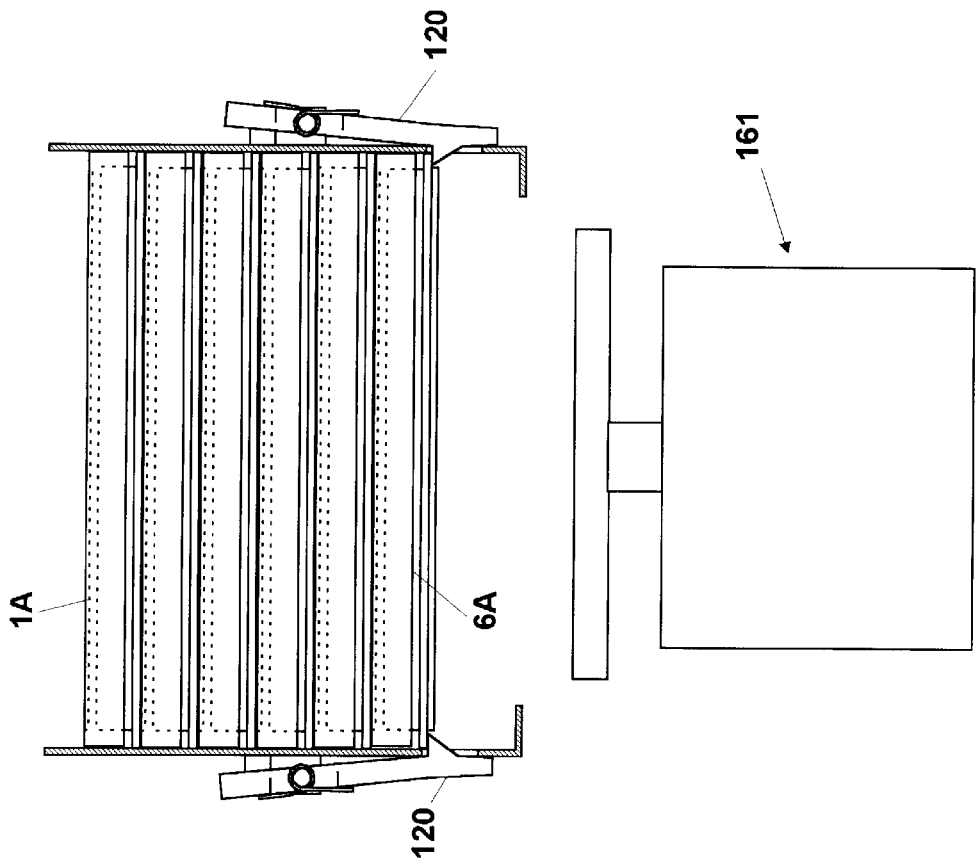

In FIG. 55, output chamber lifter 161 has lowered. Output stack A1–A6 is resting on stack support pieces 120. The space at position ε (FIG. 4) is clear to make room for the next microplate in the stack.

In a fashion similar to that described by reference to FIGS. 52–55, microplates are continually stacked in the output chambers of this preferred embodiment. The embodiment utilizing output chamber lifter 161 in conjunction with stack support pieces 120 is a preferred method of stacking because a microplate can be moved into the output chamber without sliding against or contacting the microplate that is directly above it. As shown in FIGS. 52–55, there is essentially no tipping of microplates in this embodiment. As the microplates are stacked, the base of upper microplate fits snuggly into the lid of the microplate immediately below it. This helps prevent microplates from becoming askew within the output chamber and helps prevent spillage of any solution contained within the microplates.

Although the above-preferred embodiments have been described with specificity, persons skilled in this art will recognize that many changes to the specific embodiments disclosed above could be made without departing from the spirit of the invention. For example, although a preferred embodiment for an input chamber singulator was described above, it would be possible to utilize a different input chamber lifting mechanism, provided that the mechanism was able to lift the stack of empty microplates in input chamber 15, while leaving behind a bottommost microplate at position a, as shown in FIG. 4. Those of ordinary skill in the art will recognize that a variety of pneumatic driven or motor driven lifting mechanisms could be substituted for the preferred input chamber singulator discussed above. Also, although the preferred embodiment disclosed using two compact pneumatic cylinders 52, it would also be possible to use just one. Also, although the preferred embodiments described a plurality of input chambers 15 in input carousel 3 and a plurality of output chambers 16 in output carousel 5, it would also be possible to have just one input chamber 15 and just one output chamber 16 into which the microplates would be stacked. Microplate filling assembly 6 (FIGS. 3–4) would remove empty microplates from input chamber 15, fill them and then restack them in output chamber 16 utilizing the process shown in FIGS. 10–35. Also, although it was previously described how a user of the present invention would stack empty microplates inside of input chamber 15, it would also be possible to save time by attaching pre-stacked input chambers 15 containing empty microplates onto input carousel 3. Also, although it was previously stated that in a preferred embodiment there are three vacuum cups 55 extending downward from lid lifter top 42, it is possible to modify the number of vacuum cups. For example, one large vacuum cup would work, or more than three vacuum cups would work. Also, one of ordinary skill in the art would recognize that an electrical-mechanical gripper that grabs the microplate lid would also work as a lid lifter. Therefore, the attached claims and their legal equivalents should determine the scope of the invention.

We claim:

1. An automated machine for filling a plurality of microplates, comprising:
    A) at least one input stacking chamber for stacking empty microplates,
    B) at least one output stacking chamber for stacking filled microplates,
    C) a microplate filling assembly disposed between said at least one input stacking chamber and said at least one output stacking chamber, comprising:
        1. an indexing device, and
        2. a fill mechanism in communication with a media source and positioned to insert portions of said media into the empty microplates, and
    D) an automatic control unit programmed to cause said indexing device to move empty microplates from said at least one input stacking chamber, to cause said fill mechanism to inject media from said media source into wells in the microplates, and to cause said indexing device to move the microplates to said at least one output stacking chamber.

2. The automated machine as in claim 1, wherein said indexing device is a walking beam indexer.

3. The automated machine as in claim 1, wherein said plurality of microplates each comprise a microplate lid, wherein said microplate filling assembly further comprises a lid lifter, wherein said automatic control unit is further programmed to cause said lid lifter to lift said lid off each microplate and to cause said lid lifter to replace said lid after the media is injected.

4. The automated machine as in claim 1, wherein said microplate filling assembly further comprises:
    A) an input chamber lifting mechanism for periodically lifting all microplates in said at least one stacking chamber except a bottom microplate, and
    B) an output chamber lifting mechanism for lifting all filled microplates in said at least one output stacking chamber to provide a space for recently filled microplates to be moved to a bottom position in said at least one stacking chamber.

5. The automated machine as in claim 4, wherein input chamber lifting mechanism comprises an input chamber singulator comprising:
    A) a pivotable pneumatic cylinder,
    B) a link singulator pivotally mounted to said pivotable pneumatic cylinder,
    C) a rod singulator rigidly mounted to said link singulator, and
    D) tab flippers rigidly mounted to said rod singulator,
wherein an expansion of said pivotable pneumatic cylinder causes said tab flippers to rotate downward to lower the plurality of empty microplates, wherein a retraction of said pivotable pneumatic cylinder causes said tab flippers to rotate upward to lift the plurality of empty microplates.

6. The automated machine as in claim 5, wherein said input chamber lifting mechanism further comprises an input chamber lifter positioned underneath said input chamber and operating in conjunction with said input chamber singulator to lift said plurality of empty microplates.

7. The automated machine as in claim 4, wherein said output chamber lifting mechanism is two pneumatic cylinders wherein an expansion of said two pneumatic cylinders causes a first microplate positioned above said output chamber lifting mechanism to be lifted, and a retraction of one of said two pneumatic cylinders allows a second microplate to move underneath said first microplate, and a retraction of a second of said two pneumatic cylinders causes said output chamber lifting mechanism to drop said first microplate onto said second microplate.

8. The automated machine as in claim 4, wherein said output chamber lifting mechanism comprises:
    A. a single pneumatic cylinder located underneath said output chamber,
    B. at least two stack support pieces attached to the side of said output chamber,
wherein an expansion of said single pneumatic cylinder causes a first microplate positioned above said output chamber lifting mechanism to be lifted above said at least two stack support pieces, and a retraction of said pneumatic cylinder positions said first microplate so that it is supported by said at least two stack support pieces and allows a space for the second microplate to move underneath said first microplate.

9. The automated machine as in claim 3, wherein said microplate filling assembly further comprises a linear actuator, wherein said indexing device and said lid lifter are attached to said linear actuator.

10. The automated machine as in claim 9, wherein said linear actuator comprises a lead screw, wherein said lead screw is actuated via a servo motor.

11. The automated machine as in claim 9, further comprising at least one compact pneumatic cylinder positioned between and attached to said linear actuator and said indexing device, wherein said at least one compact pneumatic cylinder is for vertical motion of said indexing device, wherein said indexing device comprises a plurality of dowel pins for pushing said plurality of microplates from said at least one input chamber, along said microplate filling assembly to said at least one output chamber.

12. The automated machine as in claim 1, wherein said at least one input chamber is a plurality of input chambers contained in an input carousel, and wherein said at least one output chamber is a plurality of output chambers contained in an output carousel, wherein said input carousel and said output carousel sequentially align said plurality of input chambers and said plurality of output chambers with said microplate filling assembly.

13. The automated machine as in claim 12, wherein said plurality of input chambers is ten input chambers and said plurality of output chambers is ten output chambers, wherein each of said ten input chambers and ten output chambers can hold twenty-four microplates.

14. The automated machine as in claim 1, wherein the automated machine is controlled by a programmable logic controller.

15. The automated machine as in claim 3, wherein said lid lifter comprises:

A) a pneumatic cylinder,
B) a lid lifter top rigidly connected to the top of said pneumatic cylinder, and
C) at least one vacuum cup rigidly connected and extending downward from said lid lifter top, and
D) a vacuum source connected to said at least one vacuum cup, wherein a retraction of said pneumatic cylinder causes said lid lifter to drop and said at least one vacuum cup to rest on said microplate lid, wherein said vacuum source transfers a vacuum to said at least one vacuum cup, wherein an expansion of said pneumatic cylinder causes said lid lifter to raise lifting said microplate lid.

16. A method for sequentially filling a plurality of microplates, said method comprising the steps of:

A) lifting via a input chamber lifting mechanism the plurality of empty microplates, wherein the plurality of empty microplates are stacked inside at least one input chamber, wherein said input chamber lifting mechanism is located adjacent to said at least one input chamber, wherein said lifting leaves behind a bottom-most empty microplate,
B) removing in sequence the plurality of microplates via a indexing device from said at least one input chamber,
C) filling in sequence the plurality of empty microplates via a nozzle, and
D) restacking via an output chamber lifting mechanism the plurality of filled microplates inside at least one output chamber, wherein said input chamber lifting mechanism, said indexing device, said nozzle, and said output chamber lifting mechanism define a microplate filling assembly.

17. The method as in claim 16, wherein said indexing device is a walking beam indexer.

18. The method as in claim 16, wherein each of said plurality of microplates comprises a microplate lid, further comprising the steps of:

A) removing in sequence via a lid lifter said microplate lids from said plurality of empty microplates after said step of removing in sequence the plurality of microplates via a indexing device from said at least one input chamber, and
B) returning in sequence via said lid lifter said microplate lids to the plurality of filled microplates after said step of filling in sequence the plurality of empty microplates via a nozzle.

19. The method as in claim 18, wherein said lid lifter comprises:

A) a pneumatic cylinder,
B) a lid lifter top rigidly connected to the top of said pneumatic cylinder, and
C) at least one vacuum cup rigidly connected and extending downward from said lid lifter top, and
D) a vacuum source connected to said at least one vacuum cup, wherein a retraction of said pneumatic cylinder causes said lid lifter to drop and said at least one vacuum cup to rest on said microplate lid, wherein said vacuum source transfers a vacuum to said at least one vacuum cup, wherein an expansion of said pneumatic cylinder causes said lid lifter to raise lifting said microplate lid.

20. The method as in claim 16, wherein said at least one input chamber is a plurality of input chambers contained in an input carousel, and wherein said at least one output chamber is a plurality of output chambers contained in an output carousel, wherein said input carousel and said output carousel sequentially align said plurality of input chambers and said plurality of output chambers with said microplate filling assembly.

21. The method as in claim 20, wherein said plurality of input chambers is ten input chambers and said plurality of output chambers is ten output chambers, wherein each of said ten input chambers and ten output chambers can hold twenty-four microplates.

22. The method as in claim 16, wherein the automated machine is controlled by a programmable logic controller.

23. The method as in claim 16, wherein input chamber lifting mechanism comprises an input chamber singulator comprising:

A) a pivotable pneumatic cylinder,
B) a link singulator pivotally mounted to said pivotable pneumatic cylinder,
C) a rod singulator rigidly mounted to said link singulator, and
D) tab flippers rigidly mounted to said rod singulator, wherein an expansion of said pivotable pneumatic cylinder causes said tab flippers to rotate downward to lower the plurality of empty microplates, wherein a retraction of said pivotable pneumatic cylinder causes said tab flippers to rotate upward to lift the plurality of empty microplates.

24. The method as in claim 23, wherein said input chamber lifting mechanism further comprises an input chamber lifter positioned underneath said input chamber and operating in conjunction with said input chamber singulator to lift said plurality of empty microplates.

25. The method as in claim 16, wherein said linear actuator comprises a lead screw, wherein said lead screw is actuated via a servo motor.

26. The method as in claim 16, further comprising at least one compact pneumatic cylinder, wherein said at least one compact pneumatic cylinder is for vertical motion of said indexing device, wherein said indexing device comprises a plurality of dowel pins for pushing said plurality of microplates from said at least one input chamber, along said microplate filling assembly to said at least one output chamber.

27. The automated machine as in claim 16, wherein said output chamber lifting mechanism is two pneumatic cylinders wherein an expansion of said two pneumatic cylinders causes a first microplate positioned above said output chamber lifting mechanism to be lifted, and a retraction of one of said two pneumatic cylinders allows a second microplate to move underneath said first microplate, and a retraction of a second of said two pneumatic cylinders causes said output chamber lifting mechanism to drop said first microplate onto said second microplate.

28. The automated machine as in claim 16, wherein said output chamber lifting mechanism comprises:

A. a single pneumatic cylinder located underneath said output chamber,

B. at least two stack support pieces attached to the side of said output chamber, wherein an expansion of said single pneumatic cylinder causes a first microplate positioned above said output chamber lifting mechanism to be lifted above said at least two stack support pieces, and a retraction of said pneumatic cylinder positions said first microplate so that it is supported by said at least two stack support pieces and allows a space for the second microplate to move underneath said first microplate.

29. An automated machine for filling a plurality of microplates, comprising:

A) a means for stacking empty microplates,

B) a means for stacking filled microplates,

C) a microplate filling assembly means disposed between said means for stacking empty microplates and said means for stacking filled microplates, comprising:

1. an indexing means, and
2. a fill mechanism means in communication with a media source and positioned to insert portions of said media into the empty microplates, and D) an automatic control means programmed to cause said indexing means to move empty microplates from said means for stacking empty microplates, to cause said fill mechanism means to inject media from said media source into wells in the microplates, and to cause said indexing device to move the microplates to said means for stacking filled microplates.

30. The automated machine as in claim 29, wherein said indexing means is a walking beam indexer.

31. The automated machine as in claim 29, wherein said plurality of microplates each comprise a microplate lid, wherein said microplate filling assembly means further comprises a lid lifter means, wherein said automatic control unit means is further programmed to cause said lid lifter means to lift said lid off each microplate and to cause said lid lifter means to replace said lid after the media is injected.

* * * * *